(12) United States Patent
LaBorde

(10) Patent No.: US 10,319,476 B1
(45) Date of Patent: Jun. 11, 2019

(54) SYSTEM, METHOD AND DEVICE FOR PREDICTING AN OUTCOME OF A CLINICAL PATIENT TRANSACTION

(71) Applicant: Brain Trust Innovations I, LLC, Tucker, GA (US)

(72) Inventor: David LaBorde, Tucker, GA (US)

(73) Assignee: Brain Trust Innovations I, LLC, Alpharetta, GA (US)

( * ) Notice: Subject to any disclaimer, the term of this patent is extended or adjusted under 35 U.S.C. 154(b) by 465 days.

(21) Appl. No.: 15/246,400

(22) Filed: Aug. 24, 2016

Related U.S. Application Data

(63) Continuation-in-part of application No. 15/004,535, filed on Jan. 22, 2016, now Pat. No. 9,569,589.

(60) Provisional application No. 62/113,356, filed on Feb. 6, 2015.

(51) Int. Cl.
| | |
|---|---|
| *G06N 3/04* | (2006.01) |
| *G06N 3/08* | (2006.01) |
| *G16H 15/00* | (2018.01) |
| *G16H 50/20* | (2018.01) |

(52) U.S. Cl.
CPC ............. *G16H 50/20* (2018.01); *G06N 3/04* (2013.01); *G06N 3/08* (2013.01); *G16H 15/00* (2018.01)

(58) Field of Classification Search
CPC .......... G06K 7/10366; G06K 7/10009; G06K 19/0723; G06K 7/10316; G06K 7/10356; G06K 7/0008; G06K 19/0717; G06K 7/10257; G06K 2017/0045
USPC ....................................................... 340/10.1
See application file for complete search history.

(56) References Cited

U.S. PATENT DOCUMENTS

| | | |
|---|---|---|
| 7,158,030 B2 | 1/2007 | Chung |
| 7,388,506 B2 | 6/2008 | Abbott |
| 7,479,887 B2 | 1/2009 | Meyer |
| 7,586,417 B2 | 9/2009 | Chisholm |
| 7,772,981 B1 | 8/2010 | Lambert et al. |
| 7,850,893 B2 | 12/2010 | Chisholm et al. |

(Continued)

OTHER PUBLICATIONS

Pivato et al., "Experimental Assessment of a RSS-based Localization Algorithm in Indoor Environment", [online], May 2010 [retrieved on Sep. 4, 2015]. Retrieved from the Internet: <http://www.researchgate.net/profile/Paolo_Pivato/publication/224146714_Experimental_Assessment_of_a_RSS-based_Localization_Algorithm_in_Indoor_Environment/links/0912f502b6b29f22ea000000.pdf>.

(Continued)

*Primary Examiner* — Mark S Blouin
(74) *Attorney, Agent, or Firm* — Culpepper IP, LLLC; Kerry S. Culpepper

(57) ABSTRACT

A system that includes a plurality of RFID tags affixed to medical items, and a plurality of data collection engine devices, client devices and backend devices. The backend devices include trained machine learning models, business logic, and attributes of a plurality of patient transactions. A plurality of data collection engines and hospital information systems send attributes of new patient transactions to the backend devices. The backend devices can predict particular outcomes of new patient transactions based upon the attributes of the new patient transactions utilizing the trained machine learning models. Using business logic and the trained machine learning models, the backend devices can also make recommendations to optimize the patient flow in healthcare provider organizations.

19 Claims, 35 Drawing Sheets
(20 of 35 Drawing Sheet(s) Filed in Color)

(56) References Cited

U.S. PATENT DOCUMENTS

| | | | |
|---|---|---|---|
| 7,852,221 B2* | 12/2010 | Tuttle | G06K 7/10346 340/10.1 |
| 7,875,227 B2 | 1/2011 | Chisholm | |
| 7,922,961 B2 | 4/2011 | Chisholm et al. | |
| 7,973,664 B1 | 7/2011 | Lambert et al. | |
| 8,097,199 B2 | 1/2012 | Abbott et al. | |
| 8,098,162 B2 | 1/2012 | Abbott et al. | |
| 8,120,484 B2 | 2/2012 | Chisholm | |
| 8,181,875 B2* | 5/2012 | Nishido | G06K 19/0701 235/451 |
| 8,212,226 B2 | 7/2012 | Chisholm | |
| 8,296,247 B2 | 10/2012 | Zhang et al. | |
| 8,478,535 B2 | 7/2013 | Jojic et al. | |
| 9,569,589 B1 | 2/2017 | Laborde | |
| 9,679,108 B1 | 6/2017 | Laborde | |
| 9,848,827 B1 | 12/2017 | Laborde | |
| 9,928,342 B1 | 3/2018 | Laborde | |
| 9,943,268 B1 | 4/2018 | Laborde | |
| 9,977,865 B1 | 5/2018 | Laborde | |
| 9,980,681 B1 | 5/2018 | Laborde | |
| 10,014,076 B1 | 7/2018 | Laborde | |
| 10,026,506 B1 | 7/2018 | Laborde | |
| 10,028,707 B1 | 7/2018 | Laborde | |
| 10,043,591 B1 | 8/2018 | Laborde | |
| 10,043,592 B1 | 8/2018 | Laborde | |
| 2010/0190436 A1 | 7/2010 | Cook et al. | |
| 2011/0291809 A1* | 12/2011 | Niemiec | A61B 5/0002 340/10.1 |
| 2013/0002034 A1 | 1/2013 | Onizuka et al. | |
| 2015/0317589 A1 | 11/2015 | Anderson et al. | |

OTHER PUBLICATIONS

Zafari et al., Micro-location for Internet of Things equipped Smart Buildings, [online], Jan. 7, 2015 [retrieved on Sep. 3, 2015]. Retrieved from the Internet:<URL:http://arxiv.org/abs/1501.01539>.

Bolic et al., "Proximity Detection with RFID: A Step Toward the Internet of Things", Apr. 23, 2015, Pervasive Computing IEEE, vol. 14 Issue:2, Published by IEEE.

Wong et al., "30 Years of Multidimensional Multivariate Visualization", [online], 1997 [retrieved on Aug. 12, 2016]. Retrieved from the Internet: <http://citeseerx.ist.psu.edu/viewdoc/download?doi=10.1.1.30.4639&rep=rep1&type=pdf>.

Erica Drazen, "Using Tracking Tools to Improve Patient Flow in Hosptals", [online], Apr. 2011 [retrieved on Feb. 15, 2018]. Retrieved from the Internet: <https://www.chcf.org/publication/using-tracking-tools-to-improve-patient-flow-in-hospitals/>.

Ann Grackin et al., "RFID Hardware: What You Must Know", RFID Technology Series, Jun. 2006.

Lyngsoe Systems, "PR34 X—Belt Loader RFID Reader User Guide", Apr. 16, 2016.

Lyngsoe Systems, "ADM User Manual", Sep. 21, 2010.

* cited by examiner

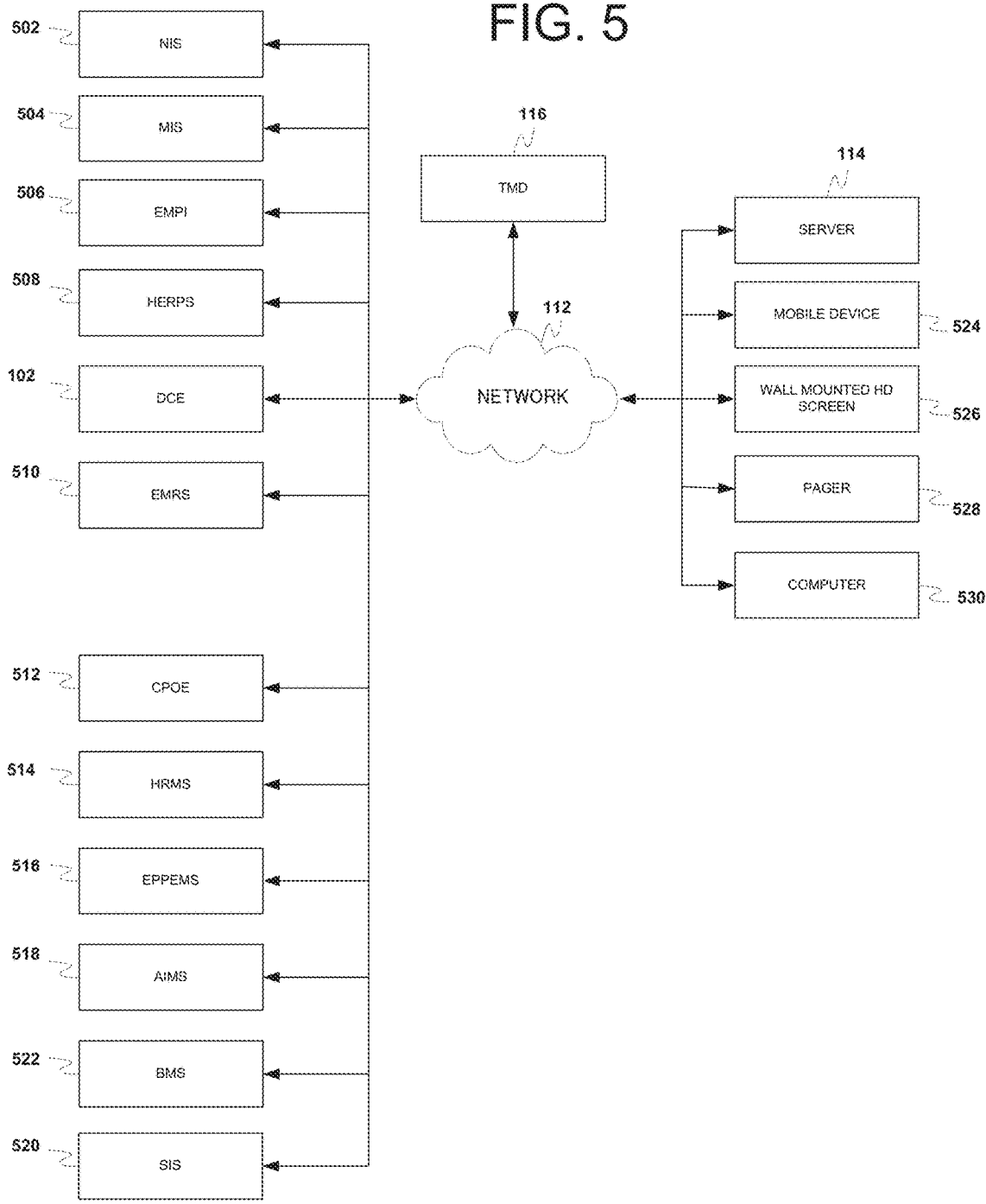

FIG. 11B

Data fields / properties

| | Property 1 | Property 2 | Property 3 | ... | Property n |
|---|---|---|---|---|---|
| Data 1 | | | | | |
| Data 2 | | | | | |
| Data 3 | | | | | |
| ... | | | | | |
| Data N | | | | | |

Collected Data

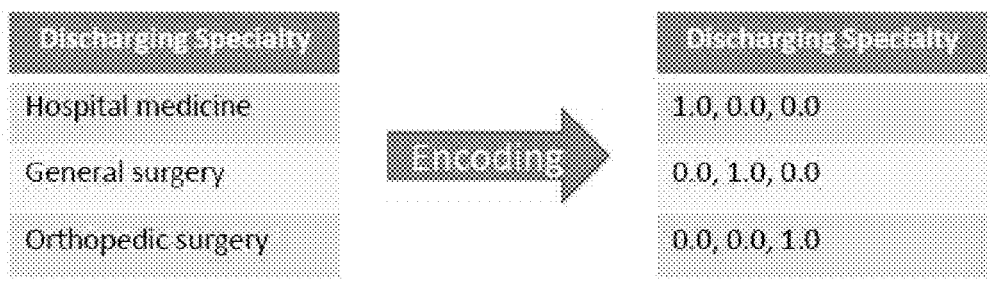
FIG. 13A
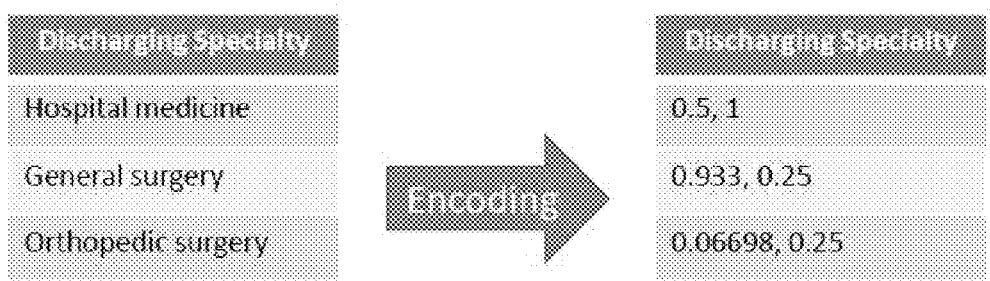
FIG. 13B
Value plotted on actual range  FIG. 12A
Equivalent value plotted on normalization scale  FIG. 12B

● BMU in a given iteration

✦ Neighborhood radius

○ Circle of influence

```
MODEL VALIDATION PROCEDURE STARTING...

Input: 1.0, 1.0, 0.0  Ideal: 0.0   Predicted: 2.99801412721799E-08
Input: 1.0, 0.0, 1.1  Ideal: 0.0   Predicted: 2.99795250960475E-08
Input: 1.0, 1.0, 1.0  Ideal: 0.0   Predicted: 2.99794721784447E-08
Input: 1.0, 0.0, 0.0  Ideal: 1.0   Predicted: 0.950920079446239
Input: 0.0, 0.0, 0.0  Ideal: 0.0   Predicted: 0.0231892518310757
Input: 0.0, 0.0, 1.0  Ideal: 0.0   Predicted: 2.99794724473062E-08
Input: 0.0, 1.0, 0.0  Ideal: 0.0   Predicted: 2.99794725297522E-08
Input: 0.0, 1.0, 1.0  Ideal: 0.0   Predicted: 2.99794721784469E-08

----- MODEL VALIDATION COMPLETE -----
```

FIG. 27
Exemplary Regression Task – Supervised Learning
(2D Example Shown for Simplicity)   ■ Actual
■ Predicted
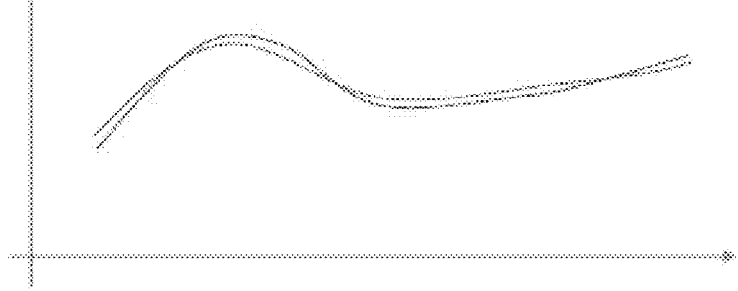
Actual vs. predicted on pre-existing data
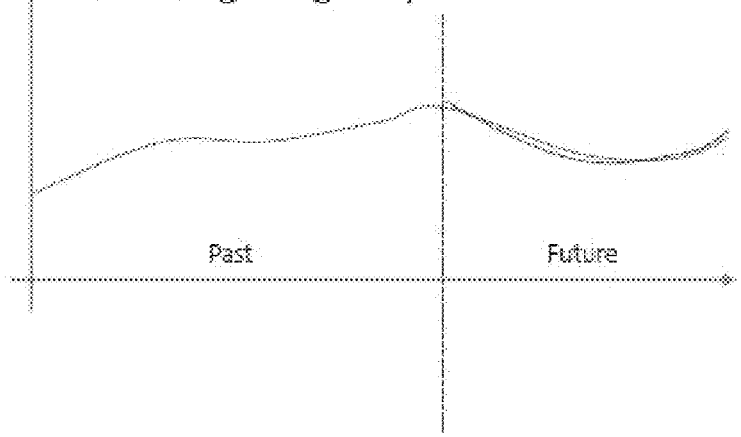
Forecasting using temporal data
Past   Future

SYSTEM, METHOD AND DEVICE FOR PREDICTING AN OUTCOME OF A CLINICAL PATIENT TRANSACTION

CROSS-REFERENCE TO RELATED APPLICATIONS

The present application is a continuation-in-part application of U.S. patent application Ser. No. 15/004,535 filed on Jan. 22, 2016, which claims the benefit of U.S. Provisional Patent Application No. 62/113,356 filed on Feb. 6, 2015, the contents both of which are incorporated herein by reference.

TECHNICAL FIELD

The technical field generally relates to a system including a data collection engine, a plurality of radio-frequency identification chips, one or more server devices, and a throughput management device. The throughput management device is configured to use a trained model to predict an outcome of a clinical patient transaction based upon patient attributes received from the data collection engine and/or radio-frequency identification chips.

BACKGROUND

Healthcare systems are complex operations in which throughput can be a major factor in the ability to accomplish goals, achieve and maintain financially solvency, and deliver a service level consistent with the expectations of customers or patients and employees, among other things. Delays or bottlenecks can have an adverse impact on throughput and reduce the performance of the healthcare system. Bottle necks can be mitigated via capacity addition and buffer allocation. However, to be able to eliminate a bottleneck, the type, location, and source of the bottleneck must first be identified.

Healthcare systems often have a finite number of assets that can potentially be deployed to mitigate bottlenecks in the system. Assets can include, for example, human capital (e.g., doctors and nurses) and will be referred to generally as resources. When presented with multiple potential bottlenecks, a challenge can be determining which potential bottleneck is most likely to be amenable to amelioration if an additional resource is deployed. Further, when such resources are limited, decisions must be made as to where to deploy the resources to best optimize the performance of the healthcare system. The most optimal resource allocation in a given healthcare system may be different from that in another healthcare system depending on the performance objectives of the healthcare system.

Conventional approaches for capturing information about the state or performance of a given healthcare system very often include measurement errors that can lead to an insurmountable barrier to obtaining the most realistic or true understanding of throughput. If a healthcare system cannot ascertain its real throughput, it will not be able to identify bottlenecks. One common source of measurement error includes employees willingly submitting inaccurate information to minimize what may be perceived to be an excessive workload.

When a patient is discharged from the hospital, while the patient's physical presence within the healthcare facility has ceased, the healthcare facilities' information systems may only become aware of this fact when a transaction consistent with the physical state of the healthcare system is entered into its bed control system. Consequently, any elapsed time between when the patient physically left the building and when the healthcare facilities' information systems are "aware" of this fact are a source of so called "invisible" or imperceptible delays which can and often do have a material impact on throughput and the performance of the healthcare system. For example, the trigger for a member of the healthcare facilities' environmental services team to be dispatched to the vacated room is this entry of the patient disposition in the bed control system. Any time between when the patient left the building and when the corresponding transaction was entered in the bed control system can be considered waste that alone or in conjunction with other waste in the system can have a real and material impact on the performance of the system. For example, if the patient room is not cleaned and "turned over" for the next patient occupant in a reasonable period of time, then a patient that could be moved into the room may still be sitting in the emergency department or the post anesthesia care unit (PACU). If there is a patient in the emergency department occupying a bed when there is no longer a need for that patient to be in that location (for example they have already been admitted to the hospital), then this means that a patient that could potentially be moved into that emergency room bed has to wait longer in the emergency room or that a patient in an ambulance that needs to bring a patient to the emergency room has to be diverted to another hospital. Or in the case of a patient in the PACU that cannot be moved out to a room on the floor, this may result in a patient that is done with surgery that cannot be transported out of the operating room because there is no bed available in the PACU, the impact of which means the operating room cannot be turned over and a patient, anesthesia team, and surgeon that could be operating on another case, cannot begin; essentially the next case that could be put in the operating room in question has to be delayed. The ultimate impact of this ripple effect can be significant. One way to think about it is the net waste in the healthcare system may result in the healthcare facilities' inability to do one or more additional surgical cases, a major source of revenue for healthcare facilities, or may result in the healthcare facilities emergency room wait times to be significantly prolonged, a major service level issue for the hospital and one that can impair the facility's brand, reputation or perception in the market place.

SUMMARY

As discussed above, information about the state or performance of a given healthcare system must be accurately captured in order to optimize throughput. Therefore, a system that can allow passive capture of information is needed.

A radio-frequency Identification (RFID) chip can transmit information to a reader in response to an interrogation signal or polling request from a reader. The RFID chip can be incorporated in a tag (RFID tag) which is placed on a medical item so that information can be passively captured. An RFID tag can be an active-type with its own power source, or a passive-type or battery-assisted passive type with no or limited power source. Both the passive-type and battery-assisted passive type will be referred to here as simply as an RFID tag for sake of brevity.

In view of the above problems, as well as other concerns, the present disclosure concerns a system for predicting an outcome associated with a new clinical patient transaction. Possible transactions include, for example, a patient transfer, patient admission, patient discharge, and patient deceased, etc. The system can be deployed for a single tenant (enterprise or private cloud deployment) and/or shared across multiple facilities (multi-tenant cloud deployment).

According to various embodiments, the system includes a data collection engine (DCE), a plurality of RFID tags, a server device, and a throughput management device (TMD).

The DCE includes a power transmission subsystem, a transceiver, a controller operatively coupled to the transceiver, and a memory including instructions for configuring the controller. The power transmission subsystem includes a power source and an antenna arranged to wirelessly transmit power to the RFID tag if it is passive-type. The transceiver can communicate with a server device via a connection to a network such as a LAN, the Internet, or cellular network and also wirelessly communicate with RFID tags. The controller is configured to generate messages to be sent by the transceiver to the server device. The DCE can also communicate with a client device such as a smartphone.

The RFID tags can be associated with, for example, an identification badge of a medical professional or a patient wrist band. The RFID tag includes an antenna for communicating with the DCE. If the RFID tag is passive-type, the antenna wirelessly receives power from, for example, the DCE, another RFID tag or the client device. The RFID tag further includes a controller configured by a memory, a microcontroller or dedicated logic for generating messages to be transmitted and a sensor group. The RFID tag can store an identification for the medical professional or patient, location data, and a time duration in which the identification has been in a particular location.

The server device includes a transceiver, a controller coupled to the transceiver, and memory portions including instructions for configuring the controller and providing one or more databases. The transceiver can communicate with the DCE via a connection to the network.

In the system, RFID tags send medical data to a DCE, the DCE transmits messages indicative of the medical data and location information to the server device, and the server device stores the medical data in one or more databases. The medical data can be patient attributes such as mentioned above.

The transceiver of the server device can be configured to receive messages from the DCE and information requests from client devices. The database can store patient transactions for patients, each including a plurality of patient attributes and a quantifiable outcome for each patient transaction such as delay time or a Boolean value (delayed or not delayed). The patient attributes can include: an age of the patient, insurance information associated with the patient, employment information associated with the patient; a medical specialty associated with a facility in which the patient is located; an individual that signed a patient transaction order and date information of the order from the memory source; a current attending physician of record for the patient from the memory source, presence or absence of a resident physician as a participant in a patient care episode, and information indicating a number of medications on a medication administration record at a time of the patient transaction.

The instructions configure the controller to: determine data in the database that is associated with the identification for the RFID tag; and store data in the message from the DCE in the database to be associated with the identification of the RFID tag.

According to a first embodiment, the instructions for configuring the controller to: create a neural network model (NNM) for modeling patient transactions; train and validate the NNM by supervised learning; calculate the outcome for new patient transactions based upon the trained NNM; classifying the output value as a risk category; and reassign resources to certain categories of the delays.

The NNM includes an input layer, one or more hidden layers and an output layer. The input layer includes a number of input neurons in accordance with the plurality of input attributes, the output layer including a number of output neurons in accordance with the quantifiable outcome, and each of the one or more hidden layers including a number of hidden layers and possibly a bias neuron. The controller is configured to initialize values of a plurality of synaptic weights of the NNM to random values and perform preprocessing of the past patient transactions, including input attributes and outcomes, consisting of zero or multiple steps (a plurality) including, but not limited to normalization and/or dimensionality reduction. Next, the plurality of past patient transactions are divided into a first set of training data and a second set of validation data.

To train the NNM, the controller iteratively performs a machine learning algorithm (MLA) to adjust the values of the synaptic weights until a global error of an output of the NNM is below a predetermined acceptable global error, wherein each of the output values represents a calculated quantifiable outcome of the respective patient transaction. Performing of the MLA includes: generating an output value of the NNM for each past patient transaction of the training data based upon the input attributes; measuring the global error of the NNM based upon the output values of the NNM and the quantifiable outcomes of the past patient transaction; and adjusting the values of the synaptic weights if the measured global error is not less than the predetermined acceptable global error to thereby obtain a trained NNM. Here, if the global error is never reached after number of outcomes, the model can be revised, such as number of hidden layers, neurons, etc.

To validate the NNM, the controller generates an output value of the trained NNM for each past patient transaction of the validation data, wherein each of the output values represents a calculated quantifiable outcome of the respective patient transaction; and determines if the output values correspond to the quantifiable outcome within the predetermined global error;

The creation and training of the NNM can be repeated until validation data results are satisfactory, defined as output data from the NNM being within the acceptable level of global error from the output values in the validation data set.

To calculate the outcome for new patient transactions based upon the trained NNM, the controller conducts preprocessing of input attributes of the new clinical patient transaction; and generates an output value of the trained NNM based upon the input attributes of the new clinical patient transaction. Finally, the TMD can classify the output value into a delay risk category to predict the outcome.

According to a second embodiment, the instructions configure the controller to create a self-organizing map (SOM) network for modeling patient transactions, the SOM including a plurality of network nodes, a plurality of input nodes representing input attributes of the past patient transactions, wherein the plurality of network nodes is arranged in a grid or lattice in a fixed topological position, each of the plurality of input nodes is connected to all of the plurality of network nodes by a plurality of synaptic weights. Creating the SOM network includes: initializing values of the plurality of synaptic weights to random values; randomly selecting one past patient transaction and determining which of the plurality of network nodes is a best matching unit (BMU) according to a discriminant function, wherein the discriminant function is a Euclidean Distance; and iteratively calculating a neighborhood radius associated with the BMU using a neighborhood kernel (function) to determine neighboring network nodes for updating, and updating values of synoptic weights for neighboring network nodes within the calculated neighborhood radius for a fixed number of iterations.

The controller can generate an output value of the SOM network based upon input attributes for the clinical patient transaction, wherein the output value is a graphical display showing a particular category for the patient transaction.

In both first and second embodiments, the controller can conduct post-processing of the output value, which can include denormalization.

The system can include the TMD, which includes a transceiver, controller and one or more memory sources operatively coupled to the controller.

The transceiver receives input attributes associated with a patient transaction from one or more remote entities via a network connection.

The one or more remote entities include: a data collection engine receiving patient identification and location information from a first RFID chip and medical professional identification and location information from a second RFID chip; a Computerized Provider Order Entry (CPOE) system; and a Hospital Bed Management System (BMS).

The transceiver further receives an information request from a remote client device via the network connection, the information request being a request for calculated quantifiable outcomes for a plurality of patient transactions. The information request can further include a request for an average discharge lag for each of a plurality of facilities in a system, each of a plurality of clinical services lines in a respective facility, each of a plurality of medical professionals, and for the system.

The one or more memory sources store instructions for configuring the controller to calculate a quantifiable outcome for each of the patient transactions from a trained model based upon at least two or more patient attributes of the respective patient transaction and classify each of the plurality of patient transactions into a delay risk category based upon the calculated quantifiable outcome and generate an information reply including a graphical display indicating the delay risk category of each of the patient transactions or the quantification (magnitude) of the predicted delay.

The information reply can include the average discharge lag for each of the plurality of facilities, each of the plurality of clinical services lines, each of the plurality of medical professionals, and for the system in the graphical display.

A client device in the system includes: a display (optional); a transceiver; a controller operatively coupled to the transceiver and the display; and one or more memory sources operatively coupled to the controller.

The transceiver sends an information request to a TMD via a network connection, the information request being a request for calculated quantifiable outcomes for a plurality of patient transactions based upon a trained model from the TMD. The transceiver receives the plurality of the calculated quantifiable outcomes from the TMD.

The memory sources storing instructions for configuring the controller to: generate a graphical display on the display indicating a delay risk category of each of the patient transactions based upon the calculated quantifiable outcomes. The memory can also store display preferences for selecting metrics to be displayed. The controller generates the graphical display to include an average discharge lag for a system and each of a plurality of subordinate hierarchical entities and members of the system based upon the display preferences stored in the memory.

Further, the controller can be coupled to a user input device and can be further configured to interact with the graphical display based upon selections received via the user input device to increase or decrease subordinate hierarchical entities displayed in the graphical display.

Generally, the backend devices (server and TMD) predict an outcome associated with a new patient transaction based upon output values from the server. The TMD and/or the server classifies the output value as one of following risk categories, low risk of delay; moderate risk of delay and high risk of delay. Based upon the classification, the TMD can allocate appropriate clinical resources to the patient transaction in accordance with the classified risk category. Finally, the backend devices and NNMs can also be employed to determine a predicted magnitude (duration) of delay, such as the predicted delay for a given patient discharge as determined upon the receipt of a discharge order.

It should be noted that all or some of the aspects of the first and second embodiments can be combined.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying figures, in which like reference numerals refer to identical or functionally similar elements, together with the detailed description below are incorporated in and form part of the specification and serve to further illustrate various exemplary embodiments and explain various principles and advantages in accordance with the present invention.

FIG. 5 illustrates an exemplary expanded operating environment in which the TMD receives medical data from the server device and various medical data sources and sends data to client devices via the network.

FIG. 11B is an illustration of an exemplary data set for patient attributes for various patient transactions.

FIG. 12A-12B are illustrations of various exemplary approaches for normalizing the data set.

FIG. 13A-13B are illustrations of various exemplary approaches for encoding the normalized data set.

FIG. 25A is an illustration of interative global error output when training a NNM.

FIG. 25B is an illustration of validation output when validating a trained NNM.

FIG. 27 is an illustration of exemplary regression tasks performed by the TMD.

DETAILED DESCRIPTION

In overview, the present disclosure concerns a system which includes a Data Collection Engine (DCE), an RFID tag associated, for example, identifications of medical professionals and patients, backend devices such as one or more server devices and a throughput management device (TMD), and a plurality of client devices.

The instant disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

Reference will now be made in detail to the accompanying drawings. Wherever possible, the same reference numbers will be used throughout the drawings to refer to the same or like parts.

Figure 1:
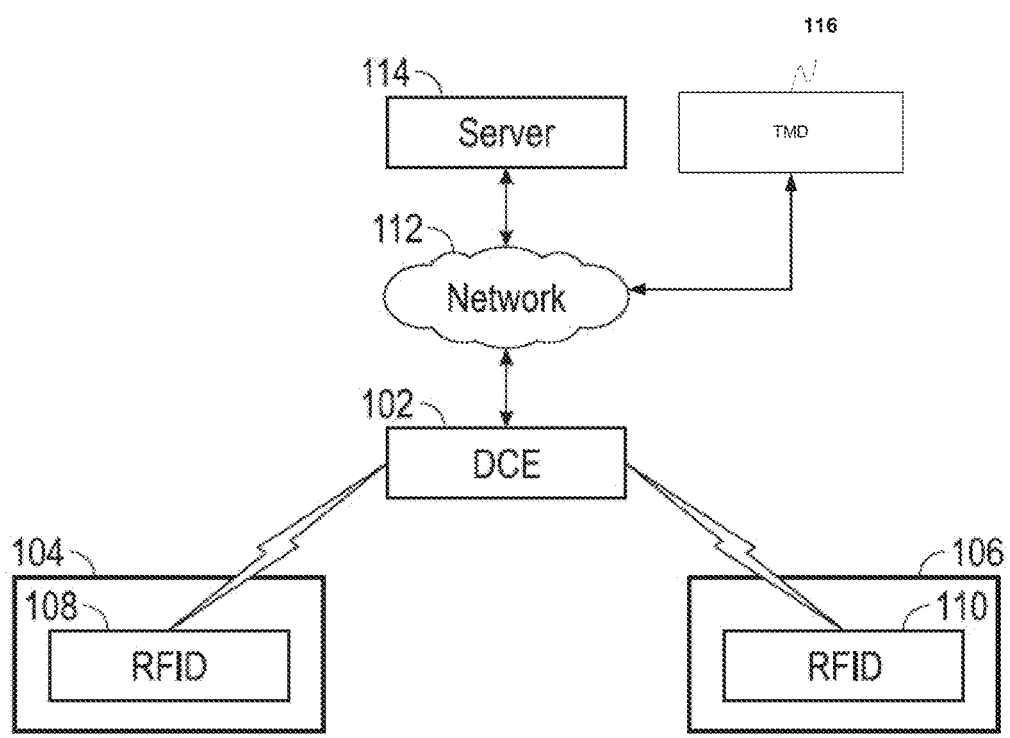
FIG. 1 illustrates an exemplary core operating environment in which a Data Collection Engine (DCE) receives medical data from RFID tags and transmits the medical data to a server via a connection to a network.
Figure 9A:
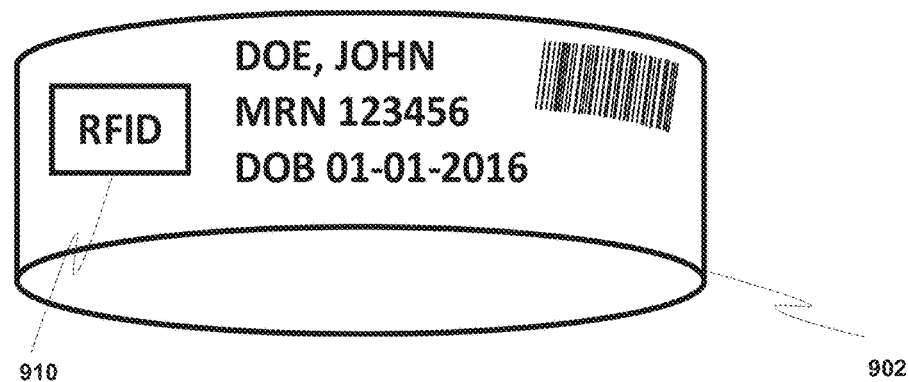
FIG. 9A is an illustration of a patient wrist band including an RFID tag.
Figure 9B:
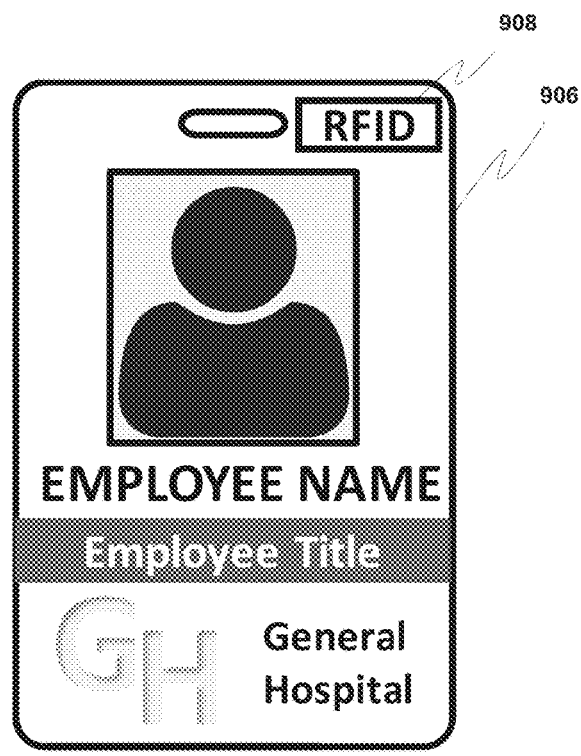
FIG. 9B is an illustration of a medical professional identification including an RFID tag.

Referring to FIG. 1, an exemplary operating environment in which the system according to various embodiments can be implemented will be discussed. The environment includes a DCE 102 communicating with first and second RFID tags 108, 110 which can be disposed in separate first and second rooms 104, 106. Each of the RFID tags 108, 110 is associated with a medical item such as a patient wrist band 902 (FIG. 9A) or doctor ID badge 906 (FIG. 9B). As discussed more fully below, the communication between the RFID tags 108, 110 and the DCE 102 is preferably wireless; however, wireline communication or a combination of wireless and wireline communication can also be used in some cases. The DCE 102, although shown here as a single entity, can include sub-portions in each of the rooms 104, 106. Moreover, as discussed later, the system likely includes many DCEs (see FIG. 6). The DCE 102 communicates with one or more server devices (represented generally by and referred to hereon as "server") 114 via a connection to a network 112 such as a local area network (LAN), wide area network (WAN), the Internet, etc. A TMD 116 can communicate with the server 114 and the DCE 102 via a connection to the network 112. The first and second rooms 104, 106 can be, for example, separate rooms of a hospital facility. The communication between the DCE 102 and the RFID tags 108, 110, between the DCE 102 and the server 114 or TMD 116, and/or between the server 114 and the TMD 116 can be encrypted or unencrypted. The network 112 can be, for example, a private LAN for the hospital facility. The server 114 can be a computing device local to the hospital facility. On the other hand, the network 112 can be the Internet, the DCE 102 can be local to the hospital facility and the server 114 can be one or more remote computing devices. One of ordinary skill in the art should appreciate that the server 114 can represent entities necessary for providing cloud computing such as infrastructure and service providers.

Figure 2:
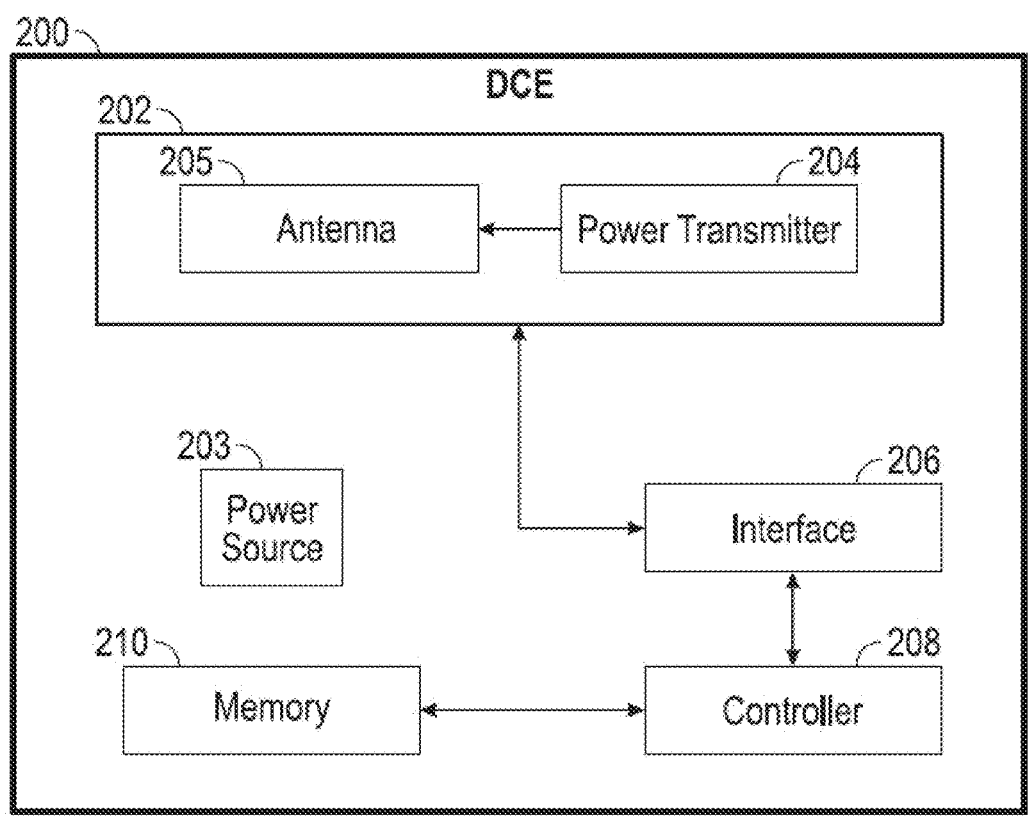
FIG. 2 is a block diagram illustrating exemplary portions of the DCE.

Referring to the block diagram of FIG. 2, portions of an exemplary DCE 200 will be discussed. The DCE 200 includes a transceiver 202, a power source 203, an interface 206, a controller 208 and one or more memory portions depicted by memory 210.

Referencing the Open Systems Interconnection reference model (OSI model), the transceiver 202 can provide the physical layer functions such as modulating packet bits into electromagnetic waves to be transmitted and demodulating received waves into packet bits to be processed by higher layers (at interface 206). The transceiver 202 can include an antenna portion 205, and radio technology circuitry such as, for example, ZigBee, Bluetooth and WiFi, as well as an Ethernet and a USB connection. The transceiver 202 also includes a wireless power transmitter 204 for generating a magnetic field or non-radiative field for providing energy transfer from the power source 203 and transmitting the energy to, for example, an RFID tag by antenna portion 205. The power transmitter 204 can include, for example, a power transmission coil. The antenna portion 205 can be, for example, a loop antenna which includes a ferrite core, capacitively loaded wire loops, multi-turn coils, etc. In addition to energy transfer, the transceiver portion 202 can also exchange data with the RFID tag. Data transmission can be done at, for example, 1.56 MHz. The data can be encoded according to, for example, Amplitude Shift Keying (ASK). The transceiver 202 includes a power transmission system composed of the antenna 205 and the power transmitter 204.

The interface 206 can provide the data link layer and network layer functions such as formatting packet bits to an appropriate format for transmission or received packet bits into an appropriate format for processing by the controller 208. For example, the interface 206 can be configured to encode or decode according to ASK. Further, the interface 206 can be configured in accordance with the 802.11 media access control (MAC) protocol and the TCP/IP protocol for data exchange with the server via a connection to the network. According to the MAC protocol, packet bits are encapsulated into frames for transmission and the encapsulation is removed from received frames. According to the TCP/IP protocol, error control is introduced and addressing is employed to ensure end-to-end delivery. Although shown separately here for simplicity, it should be noted that the interface 206 and the transceiver 202 may be implemented by a network interface consisting of a few integrated circuits.

The memory 210 can be a combination of a variety of types of memory such as random access memory (RAM), read only memory (ROM), flash memory, dynamic RAM (DRAM) or the like. The memory 210 can store location information and instructions for configuring the controller 208 to execute processes such as generating messages representative and indicative of medical data and events received from RFID tags as discussed more fully below.

The controller 208 can be a general purpose central processing unit (CPU) or an application specific integrated circuit (ASIC). For example, the controller 208 can be implemented by a 32 bit microcontroller. The controller 208 and the memory 210 can be part of a core (not shown).

Figure 3A:
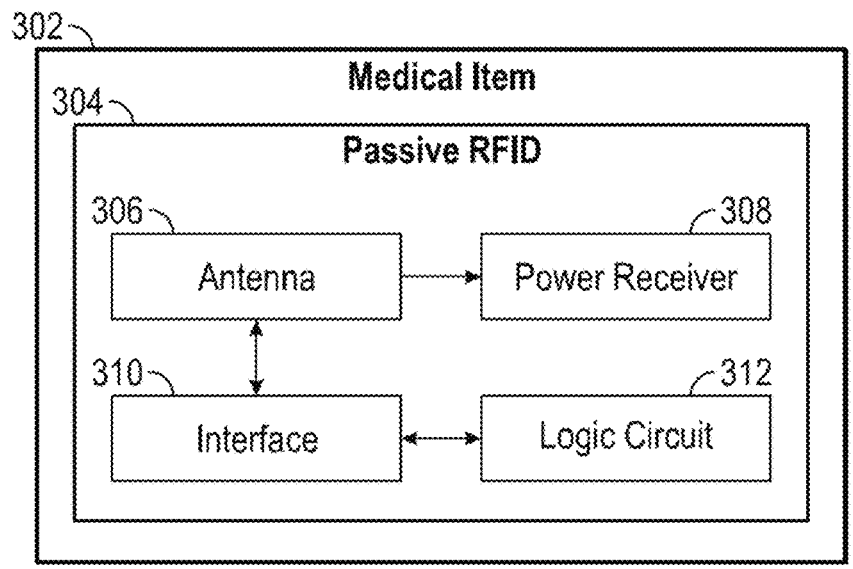
FIG. 3A is a block diagram illustrating exemplary portions of a passive-type RFID tag.

Referring to FIG. 3A, portions of an exemplary passive-type RFID tag 304 will be discussed. The RFID tag 304 can include an antenna portion 306, a power receiver 308, an interface 310 and a logic circuit 312. The antenna portion 306 can be a loop antenna which includes a ferrite core, capacitively loaded wire loops, multi-turn coils, etc., similar to the antenna portion 205 of the DCE 200. The power receiver 308 can include a power receiving coil for receiving power from the power transmission coil of the power transmitter 204 by electromagnetic coupling. The power receiver 308 can provide power to the chip 304 and/or charge a power source (not shown) such as a battery.

Generally, the logic circuit 312 generates medical data such as an identification of the RFID tag and/or the medical item to which it is affixed, state, location, and changes in any data or properties thereof over time, all of which will be referred to as medical data. It should be noted that the medical data includes situational data which refers to a) the identity of the RFID tag, the identity reference for an individual, facility plant, property, equipment to which the RFID tag is affixed, and b) the distance between an RFID tag and other RFID tags, the distance between the RFID tag and the DCE, the distance between the RFID and a client device such as smartphone, the identity and any identity references of the other RFID tags, DCEs and mobile client devices (i.e. smartphones) with which the RFID communicates, and any obtained from a sensor associated with i) the RFID tag or ii) another RFID tag, or client device (i.e. smartphone) with which the RFID communicates. Examples of the sensor data might be location in three dimensions, acceleration or velocity, displacement relative to some reference, temperature, pressure, to name a few.

The medical data can also include data indicative of an event such as, for example, near field communication (NFC) established with the DCE or another RFID tag, a time duration for which the RFID tag 304 has been within a certain location, historical data, etc. Although not shown, the logic circuit 312 can include or be coupled to a non-volatile memory or other memory sources.

The interface 310 can format a received signal into an appropriate format for processing by the logic circuit 312 or can format the medical data received from the logic circuit 312 into an appropriate format for transmission. For example, the interface 310 can demodulate ASK signals or modulate data from the logic circuit 312 into ASK signals.

Figure 3B:
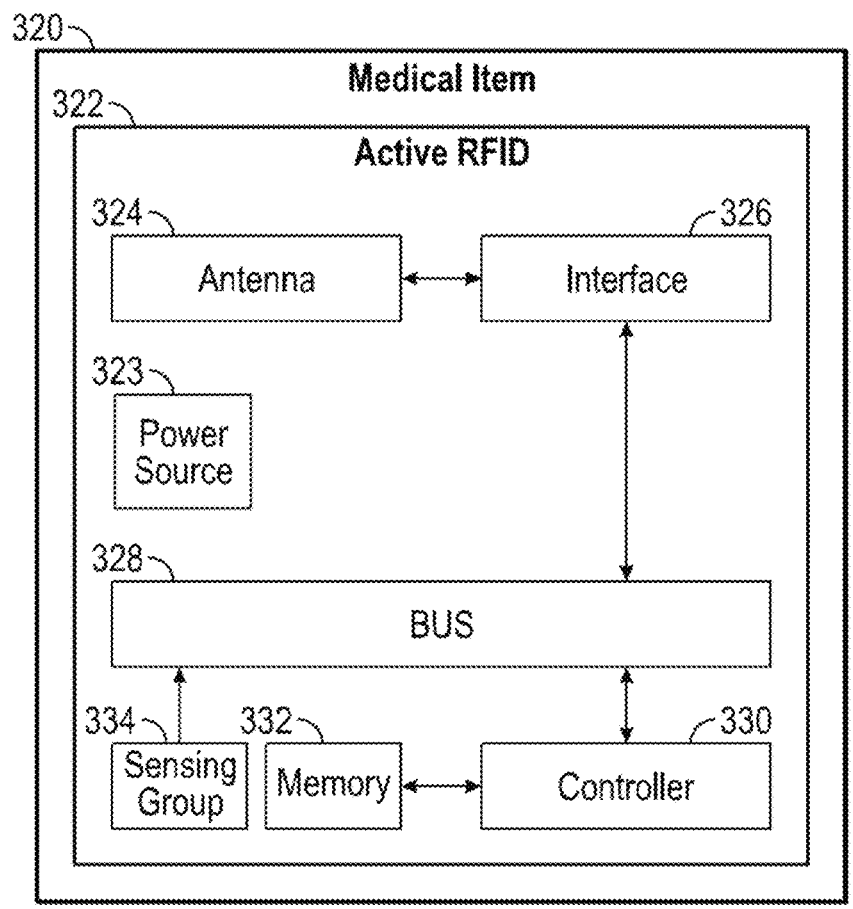
FIG. 3B is a block diagram illustrating exemplary portions of an active-type RFID tag.

Referring to FIG. 3B, circuit-level portions of the active-type RFID tag 322 on a medical item 320 will be discussed. The RFID tag 322 can include a power source 323, an antenna portion 324, an interface 326, a bus 328, a controller 330, a memory portion 332 and a sensing group 334. The power source 323 can be, for example, a battery. Although not shown, the tag 322 can also include a power management portion coupled to the power source 323.

The antenna portion 324 and interface 326 can be similar to those of the passive-type RFID tag 304. However, it should be noted that the antenna portion 324 can receive data from other passive-type and active-type RFID tags as well as the DCE and can send this and other data to the DCE, or other RFID tags.

The sensing group 334 includes sensing portions for sensing contact, motion characteristics such as an acceleration value, whether the chip is within a predetermined distance from another RFID tag, a distance from one or more other RFID tags and/or the DCE, and/or distance and angle from a baseline orientation.

The controller 330 is configured according to instructions in the memory 332 to generate messages to be sent to the DCE or another tag. Particularly, the controller 330 can be configured to send a registration message which includes identification data associated with the RFID tag 322 and thus the medical item 320. Further, in a case in which the RFID tag 322 wirelessly provides power to another passive-type RFID tag, the controller 330 can be configured to generate a message including identification data associated with the passive-type RFID tag, in combination with, or separately from its own identification data to the DCE.

The controller 330 can be configured to generate messages including medical data indicative of an event. These types of messages can be sent upon receiving a request from the DCE or another entity, upon occurrence of the event, or at regular intervals. Example events include near field communication established with another RFID tag, contact detected by the sensing group 334, positional information, a time duration of such contact and position, etc.

It should be noted that the passive-type RFID tag can also include a sensing group or be coupled to the sensing group. For example, the RFID tag 304 can be a Vortex passive RFID sensor tag which includes a LPS331AP pressure sensor. Both active and passive types of sensors can include RSS measurement indicators. As mentioned above, the DCE 102 can store data regarding its fixed location (i.e. room 106). In this case, the physical location of the RFID tag 110 can be determined via the DCE 102. Alternatively, the RFID tags can obtain position from some external reference (i.e. a device with GPS or via a device that provides an indoor positioning system location reference, or wifi hotspots, that themselves have a known location, which can somehow transmit wifi ids to the RFID chips). This later approach, involving an external device other than the DCE 102, would occur via having the other external device communicate with the RFID tag and write location data to the RFID tag memory which is then sent along with any messages to the DCE. Further, the RFID tags could also be designed to record this location information from an external source upon being interrogated by a DCE.

Figure 4A:
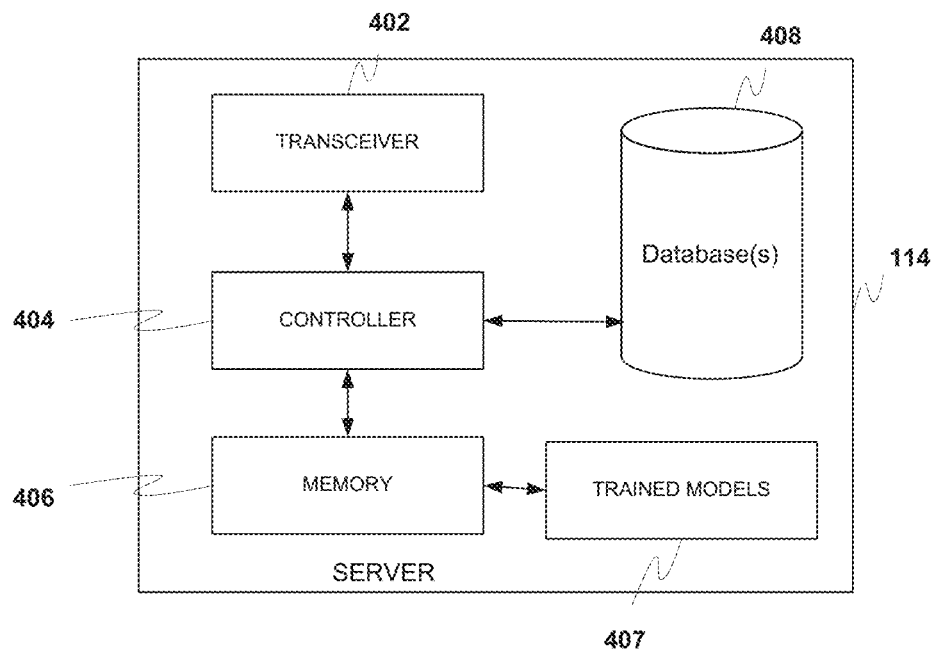
FIG. 4A is a block diagram illustrating exemplary portions of a server device.

Referring to FIG. 4A, the server 114 includes a transceiver 402, a controller 404, a first memory portion 406, a second memory portion 407 and one or more databases stored in another memory source depicted generally by 408. The transceiver 402 can be similar to the transceiver of the DCE. The transceiver 402 receives medical data via the network from the DCE, data retrieval requests from the TMD 116 and sends replies to the data retrieval requests.

The memory portions 406, 407, 408 can be one or a combination of a variety of types of memory such as RAM, ROM, flash memory, DRAM or the like. The memory portion 406 includes instructions for configuring the controller 404. The second memory portion 407 includes one or more trained models. It should be noted that the database and the trained models can be included in the memory portion 406. They are shown separately here in order to facilitate discussion.

The database 408 can include: patient identifications, attributes associated with each patient identification such as dispositions, scheduled surgeries, location history, consumed medical items, etc.; patient transactions including a plurality of input attributes and a quantifiable outcome for each patient transaction (predicted delay time and/or predicted delay categorization); a plurality of medical item identifications and usage attributes associated with each of the item identifications (the usage attributes can include an identification of a medical professional that used the medical item, an identification of a patient for whom the medical item was used, a time duration for which the medical item was in a certain location, etc); and medical professional identifications, attributes associated with each medical professional such as scheduled surgeries, location history, consumed medical items, etc.

The controller 404 is configured according to the instructions in the first memory portion 406 to determine data in the database 408 that is associated with the identification for each of the one or more RFID tags (received in the message from the DCE); store data in the message from the DCE in the database 408 to be associated with the identification of the first RFID tag; and as will be discussed more fully below, predict an outcome associated with a clinical patient transaction based upon inputting attributes of the clinical patient transaction into trained model such as a neural network model or self-organizing map network.

Figure 4B:
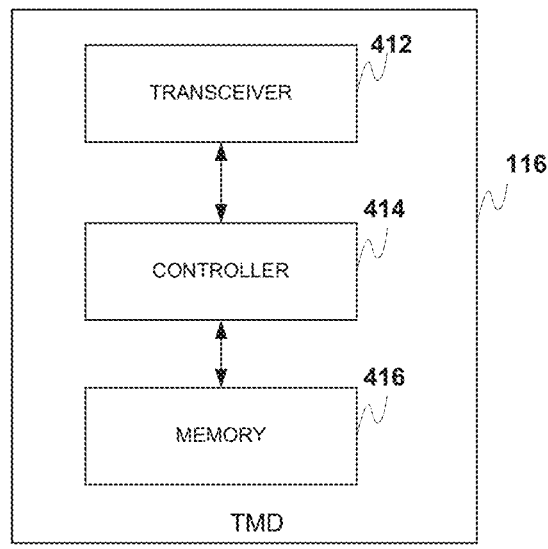
FIG. 4B is a block diagram illustrating exemplary portions of a TMD.

Referring to FIG. 4B, the TMD 116 includes a transceiver 412, a controller 414 and memory 416. The transceiver 412 can be similar to the transceiver of the DCE. The transceiver 412 receives information or resource requests such as, for example, http requests, via the network, from the client devices and other medical data storage sources. The resource request can include verification credentials such as a token issued from a certification authority (which must be determined to be valid and to contain the requisite claims for the resource being requested in order for the request to be successfully processed), and a user identifier and an information request for calculated quantifiable outcomes for a plurality of patient transactions. The transceiver 412 sends an information reply to the client device. The controller 414 is configured according to instructions in the memory 416 to generate either solely visualization data (i.e. a json object) or graphical displays (i.e. html markup and javascript) including visualization data retrieved from server 114 as the information reply that can then be used to generate a display on the client device. For example, the graphical display can indicate the delay risk category or the predicted delay duration or length (magnitude) of each of a plurality of requested patient transactions as discussed later.

In the discussion here, the server 114 and TMD 116 are shown as separate entities for ease of discussion. However, in actual implementation the server 114 and TMD 116 may be implemented within a single computing device. Moreover, the portions of server 114 may be distributed among various computing devices. For example, the trained models shown stored in memory portion 407 or the database(s) 408 could be stored at a plurality of different computing devices.

Referring to FIG. 5, an expanded exemplary operating environment is shown to illustrate how the TMD 410 communicates with various other medical data storage sources such as Nursing Information System (NIS) 502, Pharmacy Management Information System (MIS) 504, Hospital Enterprise Master Patient Index (EMPI) 506, Hospital Enterprise Resource Planning System (HERPS) 508, Electronic Medical Records System (EMRS) 510, Hospital Computerized Provider Order Entry (CPOE) system 512, Human Resources Management System (HRMS) 514, Employee Performance Planning and Evaluation Management System (EPPEMS) 516, Anesthesiology Information Management System (AIMS) 518, Perioperative Anesthesia System/Surgical Information System (SIS) 520, Hospital Bed Management System (BMS) 522 and client devices such as mobile device 524, wall mounted HD screen 526, pager 528 and a computer 530 via the network 112.

The server 114 and TMD 116 can be considered the backend devices of the system. The client devices of the system can be a desktop or fixed device, a mobile device, or another system (i.e. another backend server) that can run a native application or an application in a web browser. The various client devices contain a controller that executes instructions and a transceiver. The client devices can communicate with the backend system over the network 116 using a remote procedure call (RPC) or via Representational State Transfer (REST)-like or REST-ful architectural style or a messaging based architecture (i.e. like Health Level 7). The client devices communicate with the backend devices over Hypertext Transfer Protocol (HTTP), over another networking protocol encapsulated in Transmission Control Protocol (TCP), via message queues (for example Microsoft Message Queuing, Rabbit MQ, etc.) or any other protocols, for example, User Datagram Protocol, etc. The devices may also communicate via a cellular network (GSM, GPRS, CDMA, EV-DO, EDGE, UMTS, DECT, IS-136/TDMA, iDEN AMPS, etc.) or via other network types (i.e. Satellite phones). The data exchanged between the client devices and the backend device(s) can optionally be encrypted using Secure Sockets Layer (SSL), Transport Layer Security (TLS) and decrypted on the client device(s) and the backend device(s). The data may also be encrypted in transit using methods other than SSL/TLS (for example using a keyed-hash message authentication code in combination with a secret cryptographic key) and can be decrypted by the client or backend devices. SSL/TLS can alternatively be used in conjunction with one of the alternative encryption methodologies (belt-and-suspenders). Also, as mentioned, a client device may also consist of another third party back end system, such as another server that communicates with a database server.

Figure 6:
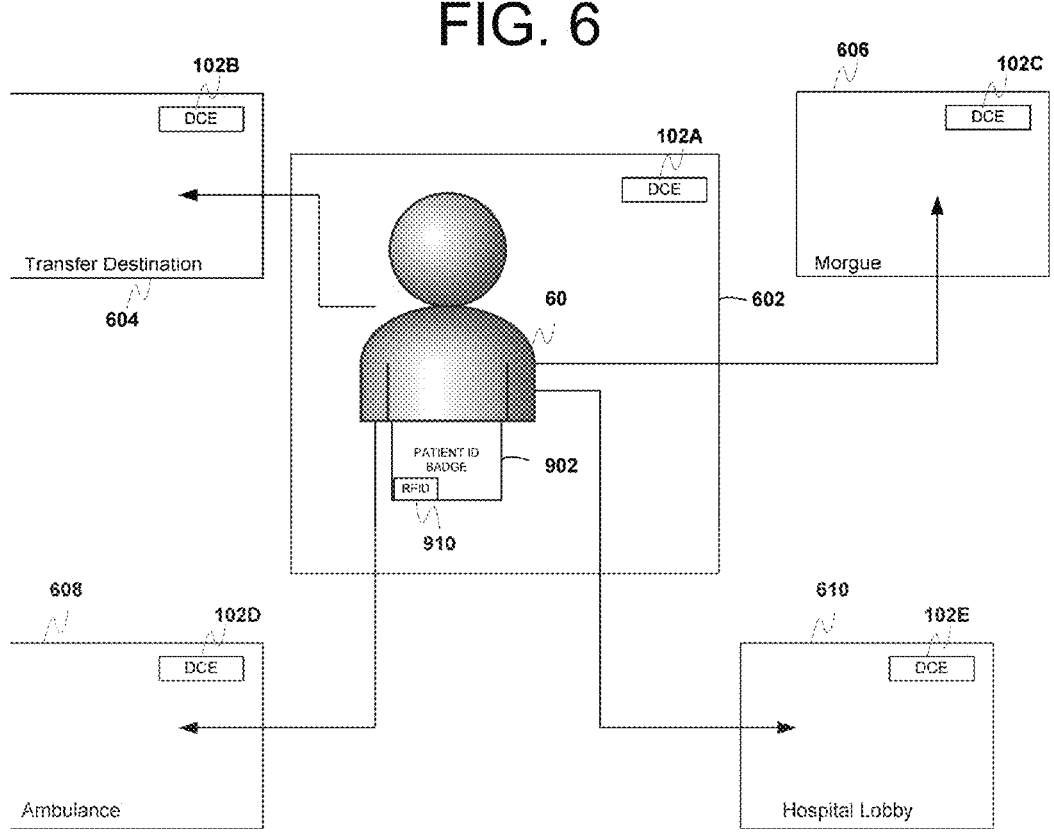
FIG. 6 illustrates exemplary patient transactions.

Referring to FIG. 6, exemplary cases of patient transactions in which the system (namely server, DCE and RFID tag) passively captures patient data will be discussed. The DCEs 102A, 102B, 102C, 102D are disposed in a position such as the ceiling beneficial for establishing wireless communication coverage for the respective room. Each of the DCEs receives medical data from the RFID tag 910 affixed to a patient identification badge 902 or a patient wristband (not shown). The DCE establishes communication with the RFID tag 910 by, for example, generating a general broadcast message, and receiving a registration message including medical data from the RFID tag 910 in reply to the broadcast message. Alternatively, the RFID tag 910 can self-initiate sending of the registration message periodically or in response to another external trigger.

Each of the DCEs 102A, 102B, 102C, 102D can store a unique identification associated with its physical location (referenced to the location, for example in a database such as 408 where the DCE IDs and locations are stored) or store a physical location when it is put into service. The identification of the DCE and/or the location information from the DCE is sent in its communications with the TMD. Accordingly, the TMD can determine the location information for the asset associated with RFID tag.

Initially, the patient 60 is in the patient room or procedure suite 602. The DCE 102A in the room 602 receives the patient identification from the RFID tag 910 of the patient badge 902.

In a first exemplary patient transaction, the patient 60 is moved from room 602 to a transfer destination room 604 such as an ICU room, step-down room, pre-op, etc. The RFID tag 910 sends a message including the patient identification and location information from the RFID tag 910 of the patient badge 902 in response to the broadcast message from the DCE 1028.

In a second exemplary patient transaction (patient deceased), the patient 60 is moved from room 602 to morgue 606. The RFID tag 910 sends a message including the patient identification and location information from the RFID tag 910 of the patient badge 902 in response to the broadcast message from the DCE 102C.

In a third exemplary patient transaction, the patient 60 is moved from room 602 to a transport area 608. The RFID tag 910 sends a message including the patient identification and location information from the RFID tag 910 of the patient badge 902 in response to the broadcast message from the DCE 102D.

In a fourth exemplary patient transaction (patient discharge), the patient 60 is moved from room 602 to hospital lobby 610. The RFID tag 910 sends a message including the patient identification and location information from the RFID tag 910 of the patient badge 902 in response to the broadcast message from the DCE 102E. Alternatively, location information could come from the DCE rather than the RFID tag in each of the four examples.

Figure 7:
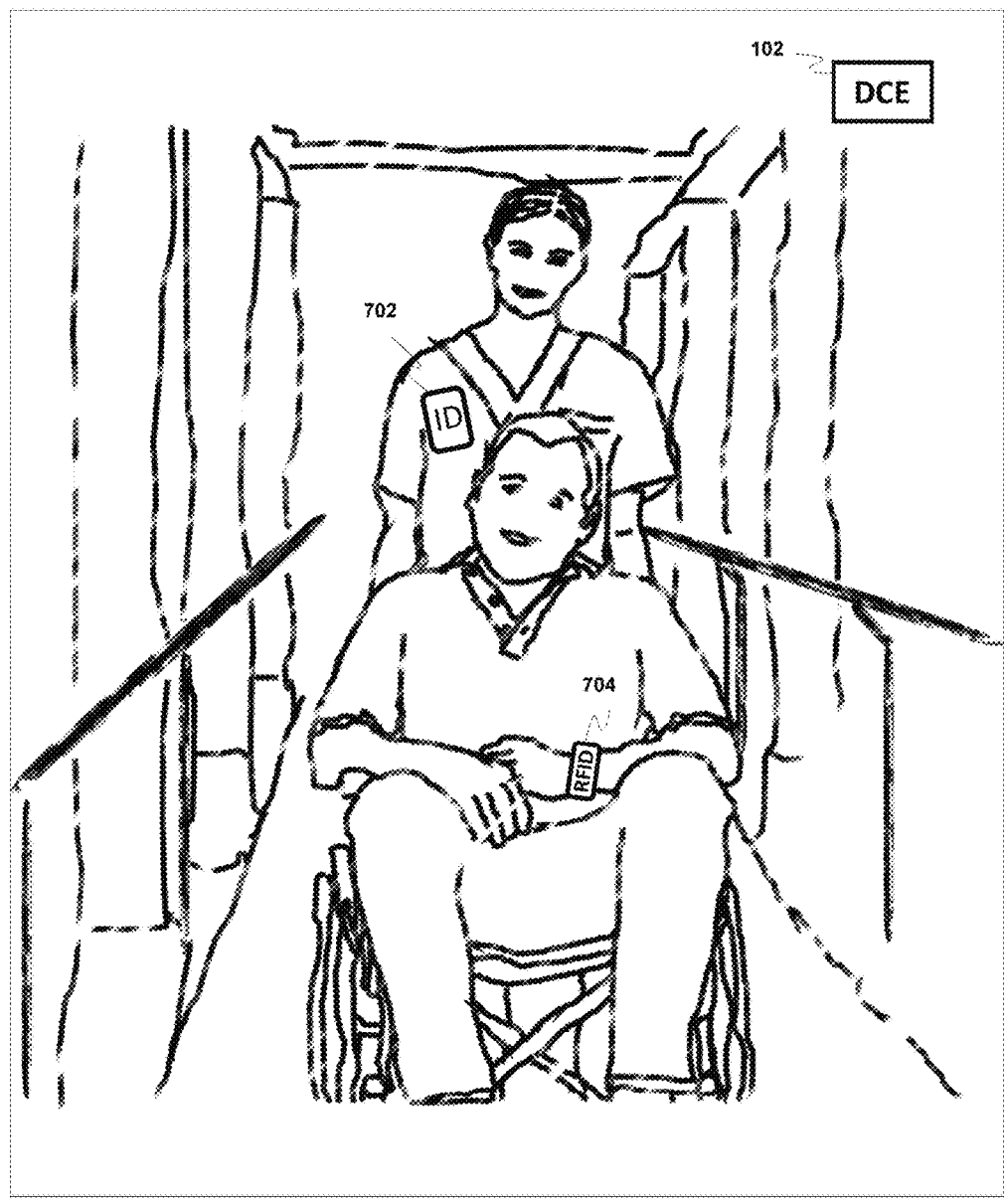
FIG. 7 is an illustration of a patient being transferred by a medical professional
Figure 8A:
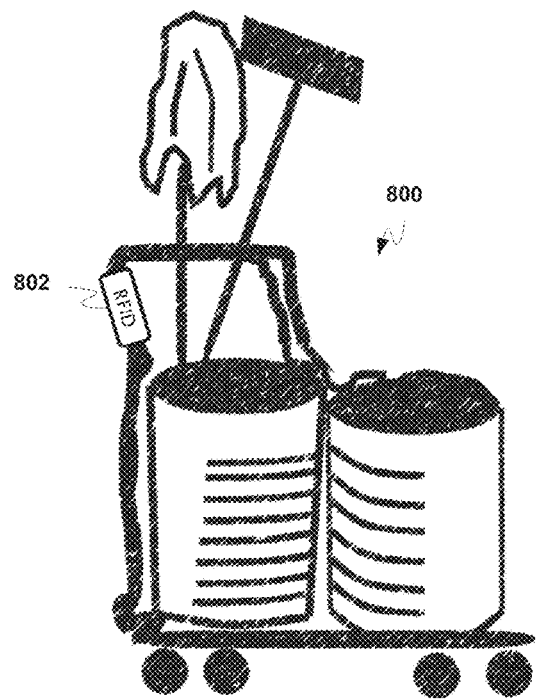
FIGS. 8A-8B are illustrations of janitorial equipment including an RFID tag and janitorial staff disposed near the janitorial equipment wearing a medical identification including an RFID tag.
Figure 8B:

In each of the four examples, the respective DCE will send the information received from the RFID tag 910 to the server device 114 via the connection to the network 112. As depicted in FIG. 7, the patient, whose wristband includes an RFID tag 704, is transferred between rooms by another medical professional who has their own identification 702 with an RFID tag that communicates with the DCE 102. Therefore, the server 114 can collect data regarding the medical professional that is transferring the patient. As depicted in FIGS. 8A-8B, after the patient has left a room (due to, for example, a transfer), the janitorial staff will enter the room to begin cleaning for turnover. RFID tags 802, 806 communicating with the DCE can include on the identification of the janitorial person 804 and the janitorial equipment 800. Therefore, the server 114 can collect data regarding the progress to room availability by collecting information about when the janitorial staff and/or janitorial equipment arrive, and when they subsequently leave the room of interest. Sever 114 can also have trained NNMs for acting on this data and data about the service line and patient that previously occupied the room to predict turn over time, or delays thereof, etc.

Only four examples of patient transactions were shown in FIG. 6. Of course numerous other types of patient transactions such as patient admission, patient transfers, and room turnovers, etc.

Figure 10:
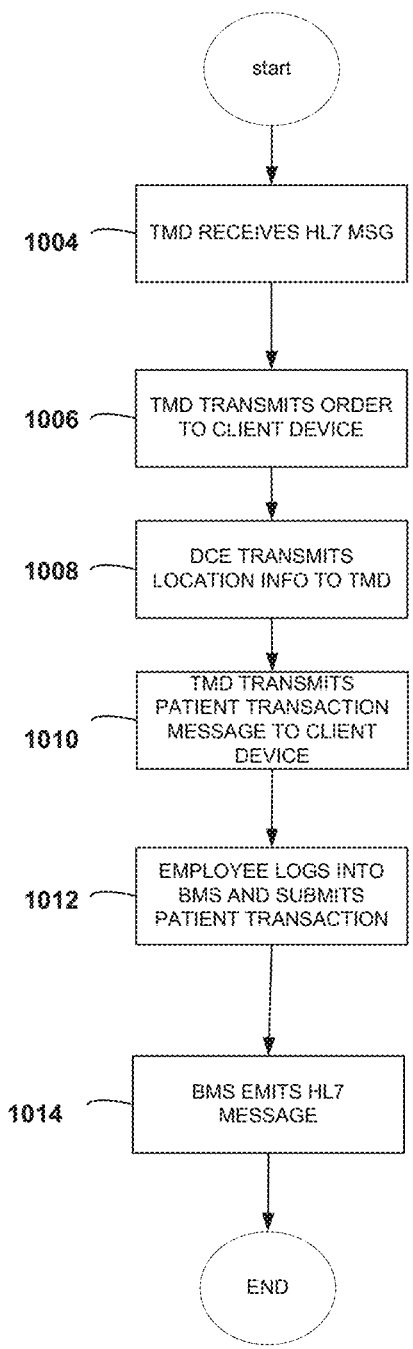
FIG. 10 is a flow diagram illustrating exemplary operations of the system during a patient discharge transaction.

Referring to FIG. 10, operation performed by entities of the system during a patient transaction will be discussed. At 1004, the TMD receives notification of an order written event (in this example, an HL7 message generated and transmitted by the CPOE system) triggered by a physician signing an order such as, a discharge patient order, an admit patient order, or a transfer patient order.

Real Time Notification of Discharge Patient Order

At 1006, the TMD transmits a notification of the order signed event to any subscribed client devices (via i.e., http, TCP, a message queue, web sockets, SMS, alphanumeric page, email, etc) such as the DCEs or client devices used in other worker processes or by hospital personnel that want real time notification of said order written events.

Predicting Discharge Order Fulfillment Delay

Consider this same discharge patient order event example: At 1004 the discharge patient order written HL7 message is received (by TMD) and the event is transmitted to any subscribed clients 1006. At this juncture, triggered by the discharge patient order written event, the TMD can initiate a call to its trained NNMs utilizing data in the system such as attributes about the patient and the patient's hospital stay, the service line the patient is on, etc. to predict the likely discharge delay categorization (i.e. not delayed, delayed, significantly delayed) and/or the likely duration (magnitude) of any predicted discharge delay.

Predicting Definitive Discharge Order Fulfilled Events

At 1008, a DCE in proximity to the patient 1006 registers the patient identification from the RFID tag of the patient wristband and transmits location information of the patient to the TMD. This process 1008 is repeated a plurality of times (not shown) to track the patient and identify any location changes (the DCE that successfully communicates with the patient's RFID chip will change as the patient is moved from the current patient room 602 to the lobby 610 (assuming for this example that the patient gets discharged home). When the TMD receives a plurality of data points from a plurality of DCEs that collectively are determined to be consistent with fulfillment of the discharge order written event, the TMD passively "knows" or determines that the patient has "physically left the building." For example, consider the following RFID derived data received from a plurality of DCEs:

1. Patient 60 left assigned room 602 with transporter,
2. Patient 60 in hallway(s) with transporter,
3. Patient 60 in lobby 610 with transporter,
4. Patient 60 no longer in lobby 610 or in facility,
5. Transporter is present in the facility, but no longer in the lobby 610, nor in proximity to patient 60

The TMD uses business logic along with its trained NNMs to predict whether a given series of data from the DCEs, such as the enumerated series of RFID to DCE messages above, are likely consistent with fulfillment of a previously received provider order written event (such as: discharge patient order, an admit patient order, or a transfer patient order) or a "turnover patient room request."

Real Time Notification of Discharge Order Fulfilled Events

Again 1008 represents a plurality of TMD/DCE/RFID communications and TMD processing of data resulting from said communications related to each provider order written event or other order written event or room turnover request it receives; detail not shown. Returning to our discharge patient order example, upon completion of 1008, the TMD "knows" the patient has been physically discharged from the facility most likely at a point in time before the Bed Management System (BMS) has been updated to reflect this "reality" and this knowledge attained by the TMD can be shared or transmitted to interested parties or processes via subscribed client devices 1010. Eventually, a worker at the hospital likely will update the Bed Management System 1012 to indicate the patient has been "physically" discharged. In fact, the TMD could be employed to actually automate the update of the room status in the BMS system (BMS would be a client device notified at 1010) removing the reliance on the human actor to keep the BMS in synchronization with "reality" and eliminating the lag between when the physical status changes ("patient has left the building") and when the BMS reflects this state change. The TMD will be notified at 1014 when the BMS has been updated to show patient 60 has been discharged from previously assigned hospital bed 602. The difference between when the TMD "knows" the patient has "left the building" 1008 and when the BMS system is updated to reflect this "reality," 1012 is potentially "invisible" waste. Invisible, because without a system like the inventive system, there is no way for the waste to be perceived from a review of data in the BMS without supplementing the data set with some form of direct observation or data derived therefrom. TMD can also be leveraged to deploy a room turnover representative (janitorial services) to vacated patient room 602 by transmitting a patient 60 in hospital room 602 has been discharged notification (to janitorial services turnover personnel with subscribed client devices at 1010) in order to have the vacated patient room turned over ("turnover patient room request"). This new "turnover patient room request" would then start a pass of the process shown in FIG. 10 anew at 1004, this time tracking the fulfillment status and providing notification of fulfillment status changes for the "turnover patient room request." This real time notification triggered at the time the actual "physical" state change occurs ("patient has left the building" then triggers "turnover patient room request") allows the hospital system to eliminate the "invisible" waste.

Predicting Room Turnover Request Fulfillment Delays and Resource Allocation

At the time the patient is discharged as determined by the TMD at 1010, the TMD, using its business logic and the requisite TMD trained NNMs, can also predict the expected delay for the room turnover activity, if any, and if needed recommend the allocation of any available resource(s) that it determines may be available and able to mitigate the likelihood that there will be a delay (waste) or to reduce the magnitude (duration) of the delay. A similar resource allocation process could be performed by the TMD in relation to discharge delays it predicts (deploying additional human capital, for example an available nurse, to facilitate and assist with the discharge and by doing so potentially mitigate the predicted waste). The TMD would be able to determine what resources may be available via communication with client devices and via communications with the other information systems in the exemplary operating environment shown in FIG. 5.

Real Time Tracking of Room Turnover Request Fulfillment Status and Continuous Machine Learning The DCE 102A in room 602 can also receive and transmit data from RFIDs 802, 806 to the TDE enabling the TMD to determine when turnover personnel (janitorial services) 804 and/or equipment 800 have entered and subsequently thereafter have left the vacated patient room 602. Note, the same process can be carried out in regards to other order requests, such as tracking arrival of transport personnel to patient room for discharge patient orders. Using this data, the TDE determines (predicts the occurrence) of the room turnover start and the room turnover complete events (which when detected would indicate fulfillment of the "turnover patient room request" at 1008) using business logic and trained NNMs the TMD has for this purpose. Furthermore, using the continuously collected "actual" data generated in the course of routine operations, the TMD's NNMs can be periodically retrained to help it better predict delays in the future. Said another way, the TMD can continuously "learn" from itself (from data sent to it from the DCEs) and in doing so be better at predicting when room turnovers will be delayed and how long the delay is likely to be. The same holds true for how the TMD can "learn" from passively collected patient discharge, patient admission, and patient transfer activity data. In essence, when the TMD's NNMs are retrained, the TMD is "studying" the historical data it collects over time and is learning, so called "continuous machine learning."

Real Time Notification of Room Turnover Request Fulfillment Event

After room turnover is "passively" determined to be complete (room turnover request is fulfilled) by the TMD and its trained NNMs, it can then emit a room turnover complete message to any subscribed client devices 1010. Upon sending such notification, a downstream process can then make use of this information, with one of the end result being the room would become available to be assigned to and receive a new patient. A hospital employee eventually will log into the BMS and update status of a room to "room turn over complete" and "room available" and TMD will receive this notification 1014. However, there likely is a difference between the time that TMD "passively" determined that the room turnover was complete as compared to when BMS "knows" the turnover is complete as the BMS only "learns" this when BMS is updated by the hospital employee to reflect that "reality." The TMD's timestamp is likely earlier as it reflects what actually occurred, whereas the BMS was reliant on a human entering the information. The difference between the two timestamps is the "invisible"

waste that is eliminated by deploying the inventive system. In fact, just as described for patient discharge order fulfillment, the BMS (as a client device to the TMD) can also be updated automatically by receiving notification from the TMD once a "turnover patient room request" has been fulfilled; this removes any dependence on a human actor to keep the BMS in synchronization with the actual "reality" of the "physical" state of the system (room turned over and available for a new patient).

If the patient transaction was a discharge patient order for a deceased patient to be moved to the morgue, the DCE would not register the patient in the assigned room 602, but in the morgue 606 with another medical professional at 1008. If the patient transaction was a patient transfer, the DCE would not register the patient in the assigned room 602, but in the new location.

In such patient transactions, there will often be a lag between the time a transaction is ordered and when the transaction is completed and reported, for example in the BMS. For a patient discharge, there is a first time period from the time the discharge is ordered to the time the discharge has been confirmed by the TMD (by, for example, registering the patient in the hospital lobby) referred to here as discharge order fulfillment lag. There is a second time period from the time discharge has been confirmed by the TMD to when the hospital employee logs into BMS and submits patient discharged transaction referred to here as completed discharge reporting lag. The total discharge lag is the sum of both time periods, that is the total time elapsed between discharge order and room status change update entry in BMS. For a patient transfer, there is a first time period from the time the transfer is ordered to the time the bed has been assigned referred to here as transfer bed assignment lag. There is a second time period from the time bed has been assigned to when the bed is available referred to here as transfer bed availability lag. There is a third time period from the time bed is available to when the transfer is fulfilled (patient is in the room as confirmed by the DCE) referred to here as transfer order fulfillment lag. There is a fourth time period from the time the transfer order is fulfilled to when the hospital employee logs into BMS and submits patient transferred transaction referred to here as completed transfer reporting lag. The total discharge lag is the sum of all four time periods, that is the total time elapsed between transfer order and room status change update entry in BMS. There are similar lags for patient transactions such as room turnover, patient admission, etc. The system according to the embodiments described can reduce these total lags by predicting delay for a patient transaction and reallocating resources accordingly.

Creating a Trained Neural Network Model to Predict an Outcome

Figure 11A:
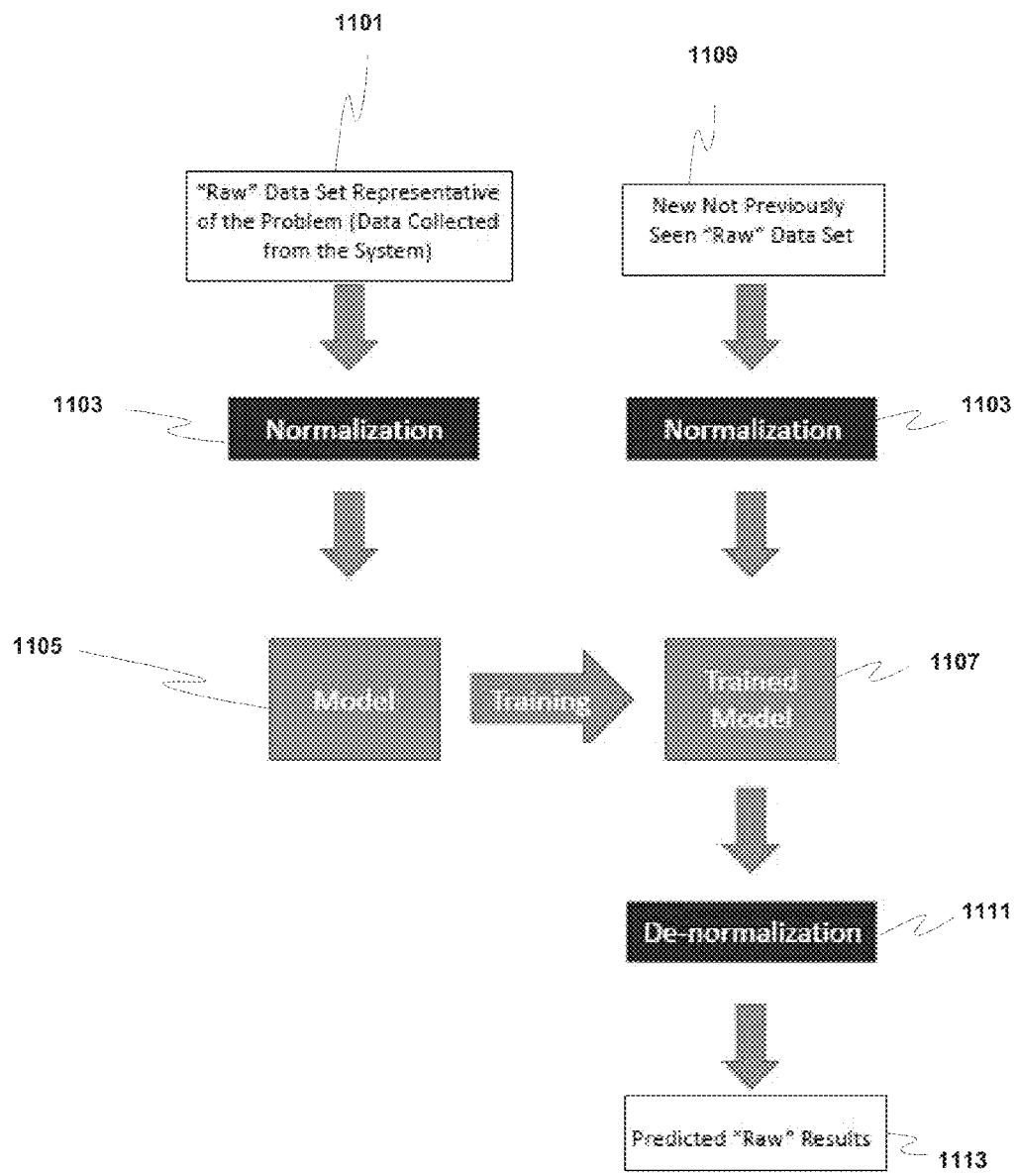
FIG. 11A is a block diagram illustrating high level operations for creating a trained neural network model (NNM) according to an embodiment.

The server device 114 stores a trained neural network model which is used to predict an outcome of a clinical patient transaction. A representation of the process for creating, training and using the trained model is shown in FIG. 11A. Raw data 1101 is normalized 1103, and then input into the model 1105. The model 1105 is trained to form the trained model 1107. New data 1109 is normalized 1103 and input into the trained model 1107. The output data of the trained model 1107 is de-normalized 1111 to obtain the output data (predicted raw results) 1113. As shown in FIG. 11B, the raw data 1101 and new data 1109 include sets of data [1, 2 . . . N] with known outcomes and properties of each of the data. For example, the data can be past patient transactions with known delay outcomes. The properties of the data can be discharge attributes.

The model 1105 is trained by an iterative machine learning algorithm. After initial deployment, the server 114 will also continuously collect data from a variety of sources along with actual related healthcare system clinical and operational outcomes; this data can subsequently be used as training data. As such, the TMD/server is able to continuously learn and improve its ability to predict the outcomes of interest. In addition, the knowledge of the system can continue to evolve in the event the system dynamics change. Take, for example, the time between when a healthcare worker signs a discharge order and the time of the patient's actual physical disposition from the facility in question. There is a relationship between the multitude of attribute data the system collects about a discharge and the outcome in question. Exemplary discharge attributes the server 114 collects about a pending discharge that can be used: the patient's age, the age of the patient's next of kin, the age of the patient's spouse, the zip code of the patients spouse and or next of kin, the patients insurance, the patients credit rating, the patients employment, the patient's current hospital ward, the discharging medical facility, the discharging medical or surgical specialty, the identity of the patients current nurse, the identity of the current charge nurse on duty, the identity of the individual that signed the discharge order, the current attending physician of record for the patient, the presence or absence of a resident physician as a participant in the patients recent hospital care, the presence or absence of a physician extender (nurse practitioner or physician assistant) as a participant in the patient's recent hospital care, the time of day the discharge order is written, the day of the week on which the order was written, the time of year the discharge order was written, the number of medications on the patients medication administration record at the time of discharge, the patient's laboratory results, the patients diagnostic imaging results, the patient's vital signs, to provide several examples. However, there is no one specific mathematical relationship or equation that describes the relationship between these exemplary attributes of the pending patient discharge and the outcome of interest (discharge lag time). However, because of the server's machine learning capabilities it has the ability to "learn" or be trained from pre-existing data and from the data it collects prospectively. Said another way, the server 114 "learns" from experience.

Data Set Encoding, Normalization and De-Normalization

Neural network models only use numerical double values for training and processing. Thus any nominal categorical data fields that are a part of raw data that will ultimately be used by models in the system are first encoded to numerical values and "raw" numerical data in many cases by a pre-processing such as normalization 1103 before training and processing. While normalization and de-normalization steps may not be explicitly described as being carried out before or after data consumption by any given model, this should not be misconstrued and lead to the assumption that these routine steps are not carried out.

The normalization processes 1103 and corresponding de-normalization processes 1111 are used not only for training data sets, but also for new, unseen data that is fed into the trained models. Though it is not the rule, frequently, the output from the trained models is normalized and in the event it is a categorical data field the output will also be encoded. Thus, often output from the system models has to be de-normalized and possibly decoded to yield the "raw data," "human readable" format of the predicted output.

Neural network training is often more efficient when independent numeric data (x-data) is normalized. For this reason, the system most often normalizes numeric data along the same scale being utilized by the model for all data fields, including nominal data fields. The scale the system utilizes for normalization depends on the particular activation function employed by a given model. In most cases this results in normalization either from −1 to 1 or 0 to 1, however, in some cases intermediate range values may be used as well, such as −0.5 to 0.5, for example. This "raw data" normalization step also prevents predictors or inputs that are relatively larger in magnitude (as compared to other predictors or inputs) from having more relative influence on the change in the value of synaptic weights during training of the system models. For problems with normalized nominal data, one neuron is required to represent each numeric data field type.

An example of one of the independent predictors (input x-data) or discharge attributes that can be utilized by the system is the number of medications a given patient is prescribed at the time of discharge. Suppose a patient has 19 discharge medications and that this "raw data" value needs to be normalized to a −1 to 1 normalization range. If the actual range of the possible number of discharge medications is 0 to 50, for example, then to normalize this input x-data, the system's continuous or numeric normalization process would carry out normalization calculations similar to those illustrated herein. Initially, the value can be plotted on an actual range as shown in FIG. 12A. Then a normalization calculation can be carried out as shown below:

$$\{[(19-0.0)*(1.0-(-1.0))]/(50.0-0.0)\}+(-1.0)=-0.24$$

Referring to FIG. 12B, equivalent value plotted on a normalization scale is shown.

In the encoding process, the system may encode classification labels into double values within the normalization range such as −1 to 1 or 0 to 1. The scale the system utilizes for encoding depends on the particular activation function employed by a given model. An approach the system employs at times to encode nominal data fields is so called one-of-N encoding as shown in FIG. 13A. For example, one of the attributes that may be used is the discharging medical or surgical specialty. In this case the hospital has three medical and surgical specialties that discharge patients: hospital medicine, general surgery and orthopedic surgery. The nominal categories are represented by double values within a normalization range of 0 to 1. Another variety of this approach that can be used is one-of-C-dummy encoding. When this method is employed, the number of neurons needed to represent a given number of nominal data field types is equal to the number of distinct nominal categories. However, one-of-N encoding is subject to an unequal distribution of error (unequal fault behavior) for wrong predictions which can occur when there are more than two nominal categories. For example, if the value predicted by a given model is orthopedics {0.0, 0.0, 1.0} but the ideal (real) value is actually general surgery {0.0, 1.0, 0.0}, it is apparent that there is only error in two parts. Said another way, if the predicted and the ideal (real) values are compared, the first value is 0.0 in both (i.e. is correct), while the other two values are both wrong. This is unequal distribution of errors.

Due to this shortcoming of one-of-N encoding, particularly in instances when there are more than two nominal categories, the server can employ equilateral encoding (one-of-(N−1) encoding shown in FIG. 13B or one-of-(C−1) dummy encoding for encoding nominal categorical data. When equilateral encoding is used fault behavior is equally distributed when wrong predictions are encountered. The equilateral encoding used by the system is based on the Euclidean normalization technique which results in each nominal category having equal Euclidean distances from the others. The Euclidean Distance is calculated as shown below:

$$\text{distance} = \sqrt{\frac{(i_1 - a_1)^2 + (i_2 - a_2)^2 + \ldots + (i_n - a_n)^2}{n}}$$

Where the variables represent the following:
i=ideal (real) output value
a=actual (predicted) output value
n=number of sets of ideal and actual values With equilateral encoding, all classes are able to be represented by a number of doubles equal to one minus the total number of nominal data classes, in this case 2 (3−1=2). When this technique is used, every set of possible ideal and actual combinations in the above example will result in an equivalent Euclidean distance.

Ideal: {0.5, 1} Actual: {0.933, 0.25}
Euclidean Distance:
=$((0.5-0.933)^2+(1.0-0.25)^2)^{1/2}$
=$(-0.433^2+0.752^2)^{1/2}$
=$(0.187489+0.5625)^{1/2}$
=$(0.749989)^{1/2}$
=0.8660
Ideal: {0.06698, 0.25}
Actual: {0.5, 1}
Euclidean Distance:
=$((0.06698-0.5)^2+(0.25-1)^2)^{1/2}$
=$(-0.433022+(-0.752)^2)^{1/2}$
=$(0.1875063204+0.5625)^{1/2}$
=$(0.7500063204)^{1/2}$
=0.8660

Equilateral encoding is not employed by the system in scenarios where there are less than three distinct nominal categories.

Exemplary embodiments of a supervised and unsupervised neural network training algorithm used to create a trained model will be discussed. However, these embodiments are merely examples. Those skilled in the art know any variety of machine learning algorithm approaches can be used for the purpose of training system models including, but not limited to support vector machines, genetic programming, Bayesian statistics, decision trees, case based reasoning, information fuzzy networks, clustering, hidden Markov models, particle swarm optimization, simulated annealing, among others. While the exemplary embodiments herein do not detail every machine learning approach employed by the system to solve the technical problem, this should not be construed as an omission of these capabilities or approaches which the system can and in some case does leverage to solve the technical problem.

There are three primary categories of machine learning tasks: classification, regression and clustering tasks.

Classification

Figure 26A:
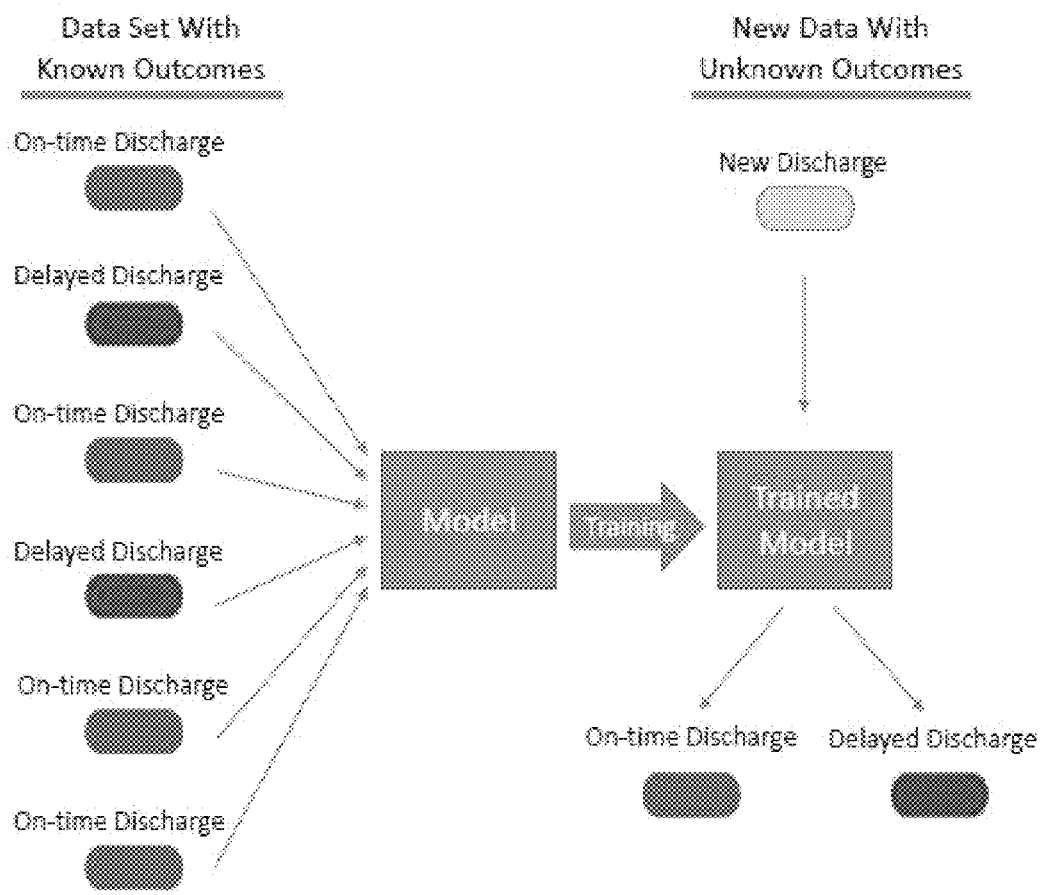
FIGS. 26A-26B are illustrations of a case in which the model is used to categorize the delay risk of a plurality of patient transactions.
Figure 26B:
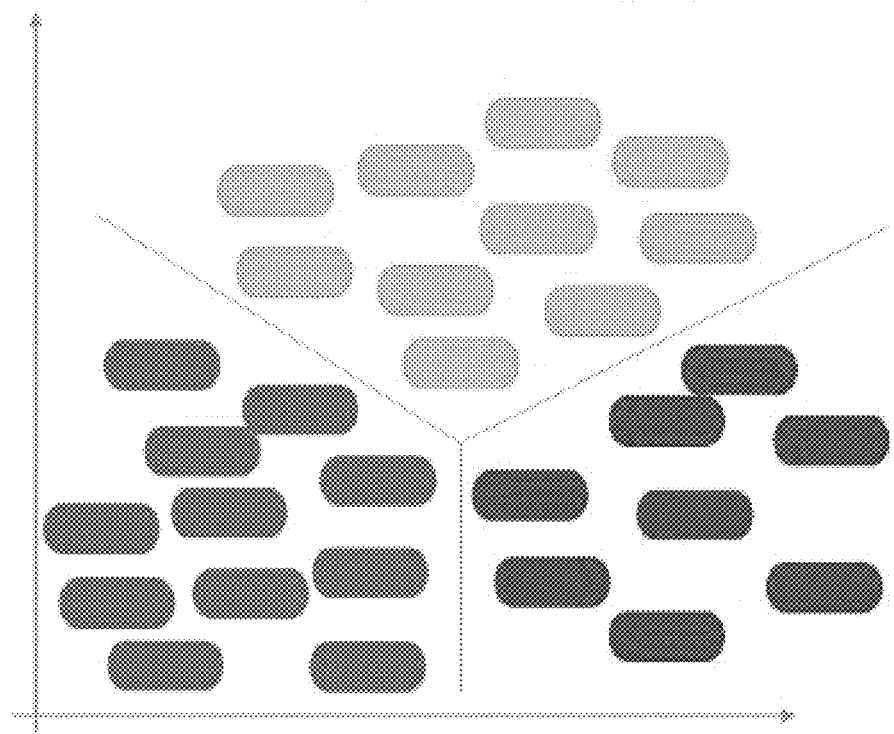

Referring to FIG. 26A-26B, a classification task for predicting delay risks of a discharge is shown. The machine learning task entails a two-step supervised learning process which utilizes both input and output data in the model training process. Model construction is done using a representative training data set and the model, once trained is used for classifying new or unseen cases, for example a discharge at risk of delay—predicts nominal categorical assessment or assignment. The inputs are collected discharge data attributes/properties. The output will be predicted categorical risk for discharge delay, not delayed, moderately delayed and severely delayed.

Regression

Referring to FIG. 27, a regression task entails a two-step supervised learning process which utilizes both input and output data in the model training process. Model construction is done using a representative training data set and the model once trained, is used to predict the output (numerical or continuous data) for new or unseen cases. The output can be, for example the anticipated length or duration of discharge delay (a quantity of time).

Clustering

Clustering tasks carried out in the server entail an unsupervised learning process. For clustering tasks, categories and outcomes are not known, or if known are not used for model training. Models are trained from the inputs of the data set, again without or ignoring the corresponding outputs, and from these the model training algorithm tries to identify similarities among the input data and cluster the data based on these learnings, so called "unsupervised learning." The backend devices employ each of these categories of machine learning tasks.

Unsupervised Learning

The server 114 in some instances utilizes unsupervised learning techniques (for example Self-Organizing Map (SOM)—also known as Kohenen Map, Singular Value Decomposition (SVD), and Principal Component Analysis (PCA)) for the purpose of dimensionality reduction. This is done to reduce the input data sets from a large number of dimensions to a lower number of dimensions, such as, for example, to two or three dimensions. This is often employed as a pre-processing step in advance of the application of supervised learning methods. By leveraging unsupervised learning for the purpose of dimensionality reduction, the system is able to reduce the processing (training) time and improve model accuracy. Some supervised machine learning techniques work very well on data sets with a low number of dimensions, however, when there are a very large number of dimensions, performance can degrade, the so called "curse of dimensionality." Thus, the employment of dimensionality reduction techniques actually boosts model performance and efficiency for some tasks.

Another exemplary task, for which the server 114 uses unsupervised learning, as detailed further later herein, is data visualization. Humans are quite facile with the visualization of data in two or three-dimensional space, however visualizing data with more than three dimensions is not a task for which humans are well suited. One of the ways the system overcomes this is by using its unsupervised learning dimensionality reduction capabilities to make patterns in n-dimensional data more easily perceptible to human end users. Thus, the server's dimensionality reduction techniques significantly boost its ability to make data actionable by making the visibility of meaningful, yet complex patterns, more perceptible to its human end users.

Supervised Learning

The backend devices can use supervised machine learning techniques.

Figure 14:
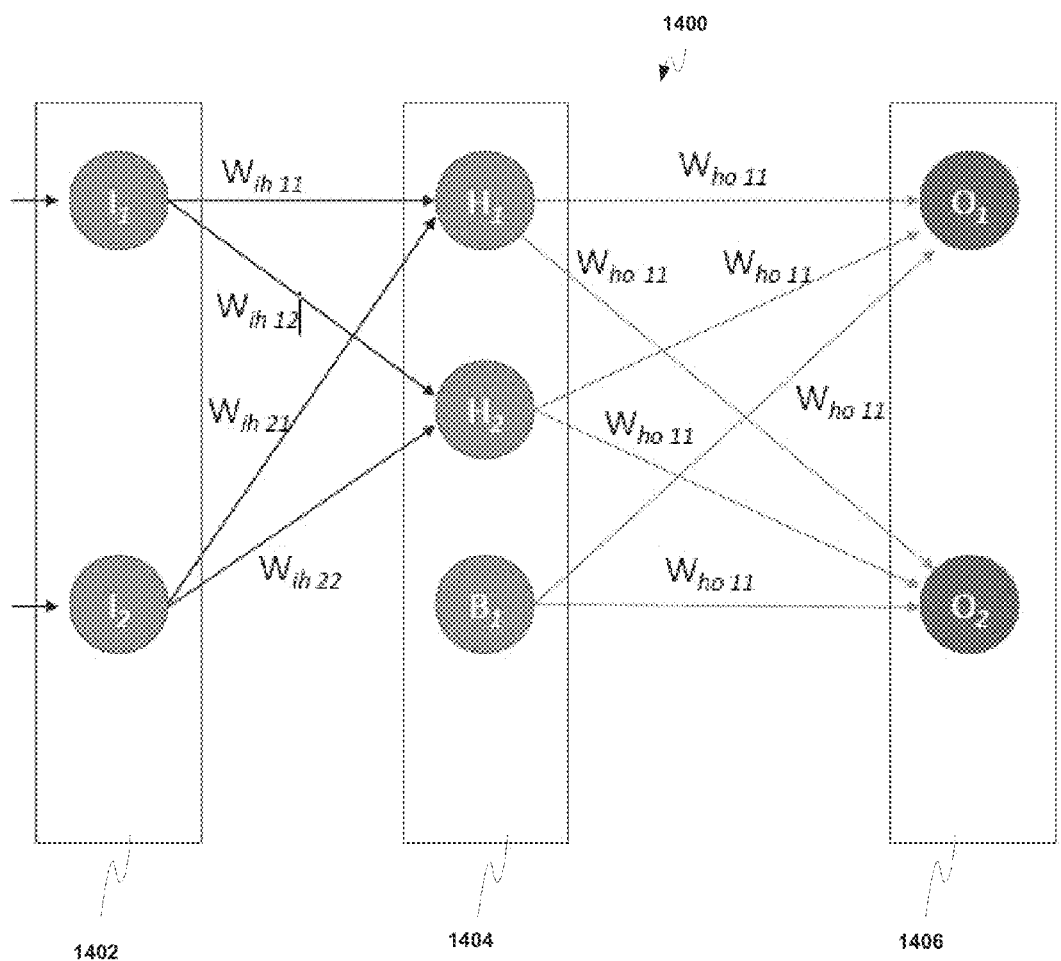
FIG. 14 is an illustration of an exemplary simple feed forward NNM.

Referring to FIG. 14, the backend devices can use a neural network model (NNM) 1400. The NNM 1400 includes an input layer 1402, a hidden layer 1404 and an output layer 1406. The input layer 1402 includes input neurons ($I_1$ and $I_2$) which provide input signals to the network without any processing units (processing units, described further herein are comprised of summation and activation functions). The hidden layer 1404 includes hidden neurons ($H_1$ and $H_2$) which provide a means to converge the network's solution leveraging additional processing units (summation and activation functions). At times, if these neurons are not present, the neural network may not be able to output the desired result. The hidden layer 1404 can also include bias neurons ($B_1$) to provide bias values if there is a requirement for non-zero results. Essentially, they provide a way to obtain a non-zero result even if the input is zero. These most typically do not have any incoming connections, but rather instead, their input values are fixed, for example being fixed with a value of one (1). The output layer 1406 includes output neurons ($O_1$ and $O_2$) containing processing units (summation and activation functions) which provide the means for obtaining the final output of the neural network. A typical neural network employed by the system is comprised of one input layer, one output layer and a plurality of hidden layers (zero or more). The number of neurons the system employs in its neural network input and output layers varies.

In the neural network, connections between neurons have a connection weight or synaptic weight, for example the connection between $I_1$ and $H_2$ has a synaptic weight of $w_{ih\ 12}$. The $w_{ih\ 12}$ notation means the synaptic weight of the connection from input neuron $I_1$ and hidden neuron $H_2$. This synaptic weight denotes the strength of the connection, the higher the weight the higher the strength and vice versa. This synaptic weight determines the effect the synapse has on processing. The synaptic weight is also directional. Said another way, this means the connection from $I_1$ to $H_2$ is different from that from $H_2$ to $I_1$. Thus the notation $w_{ih\ 12}$ not only denotes the neurons that are connected or involved but also the direction of the connection.

Figure 15:
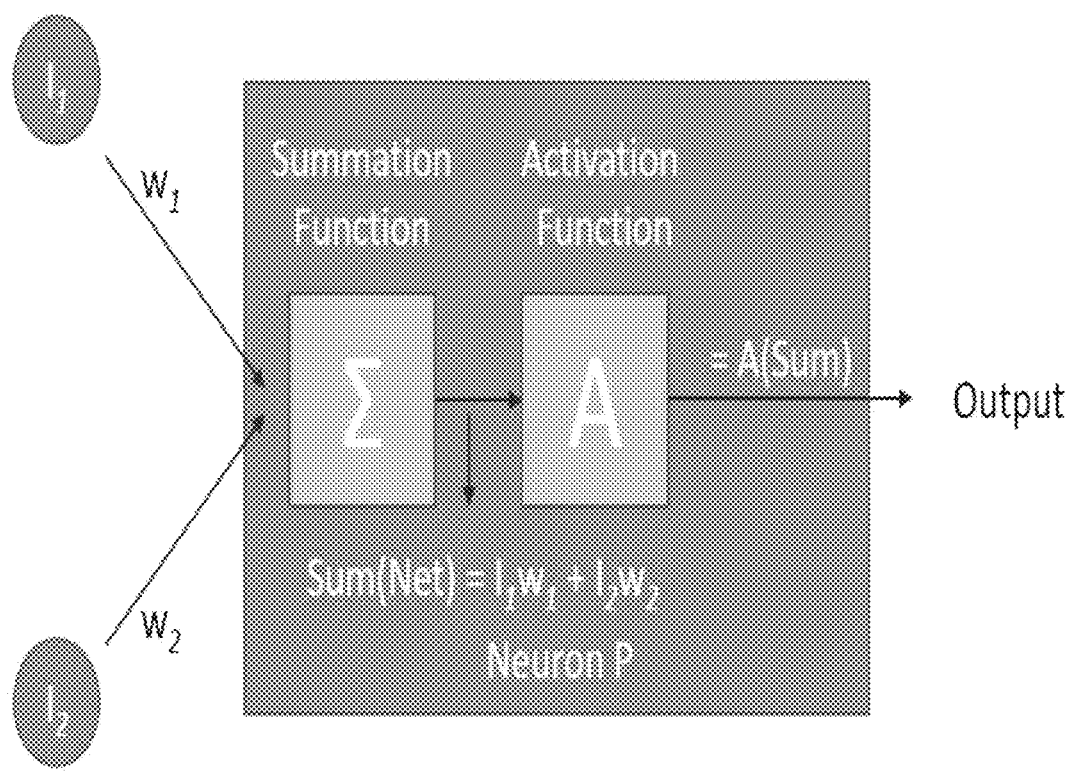
FIG. 15 is an illustration of an exemplary neuron of the NNM.

As shown in FIG. 15, a neural network neuron includes the summation function and activation function. The summation function sums input signals based on their signal strength, or weights. The sum value is also known as Net. The output of the summation function is the weighted sum of input signals. The activation function of a neuron takes the weighted sum of the input signals and performs some calculations to arrive at the output value. Some examples of activation functions used by the system include:

The sigmoid function $$f(x) = \frac{1}{1+e^{-x}}$$

Figure 16A:
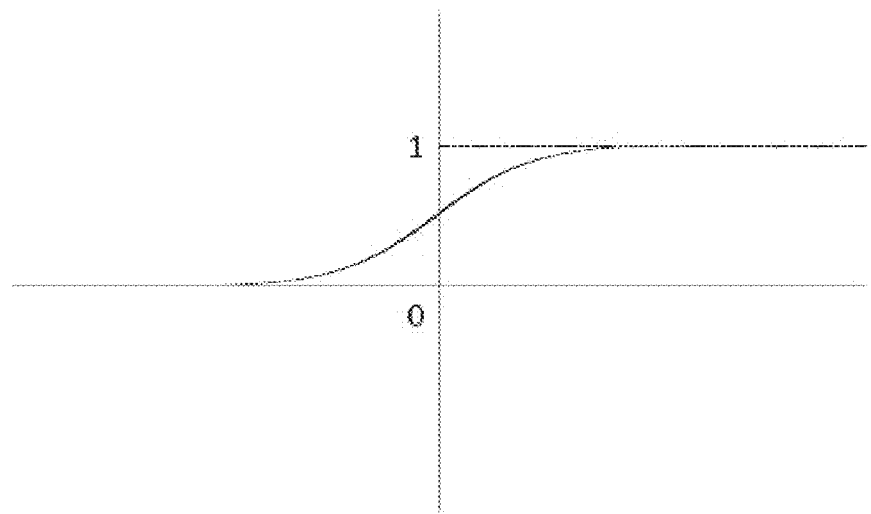
FIGS. 16A-16C are illustrations of exemplary activation functions for the neurons of the NNM.

As shown in FIG. 16A, a characteristic of the sigmoid function is that for all values on the x axis, the function output value (y axis) will lie between 0 and 1. The sigmoid function is used in instances where only positive outputs are expected.

The hyperbolic tangent function $$f(x) = \frac{e^{2x}-1}{e^{2x}+1}$$

Figure 16B:
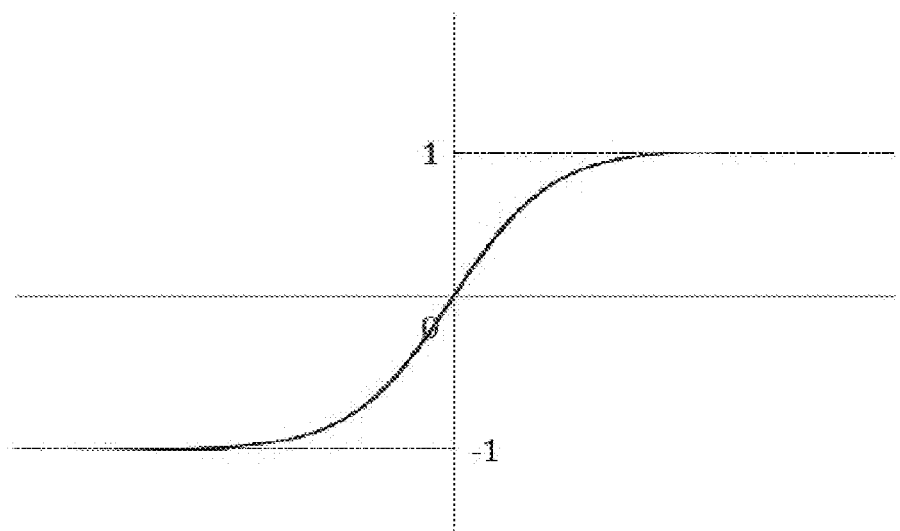

As shown in FIG. 16B, a characteristic of the hyperbolic tangent function is that for all values on the x axis, the function output (y axis) will lie between −1 and 1. The hyperbolic tangent function is used by the system in instances when both positive and negative outputs are expected.

The linear function $$f(x)=x$$

Figure 16C:
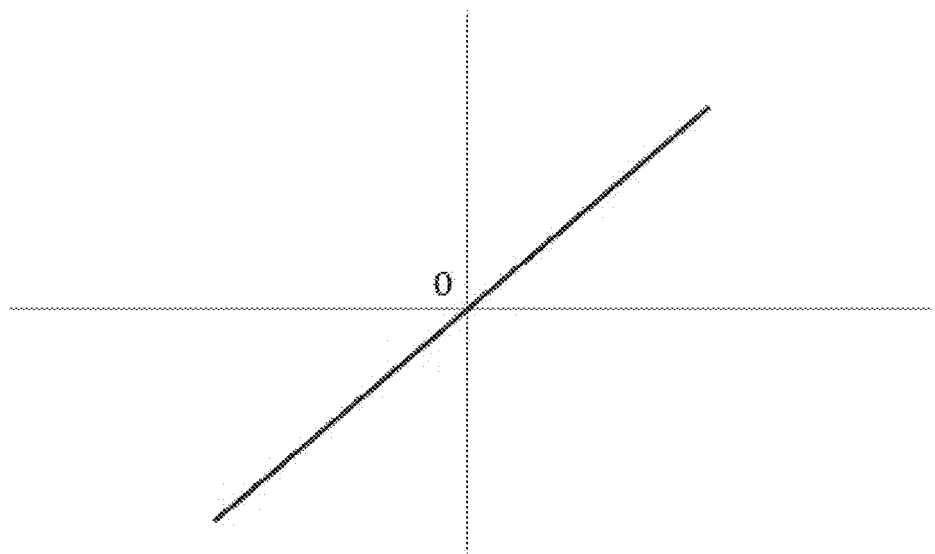

As shown in FIG. 16C, a characteristic of the linear function is that the input and output are the same. The linear function is used by the system in instances where the objective is to replicate the input signal to the output.

The activation functions detailed above are exemplary of activation functions used by the inventive system. One skilled in the art will understand that there are also other activation functions that can be used in neural networks. This disclosure is not intended to be exhaustive, but is intended to describe the fact that the server 114 employs a plurality of activation functions to accomplish its objectives.

Figure 17:
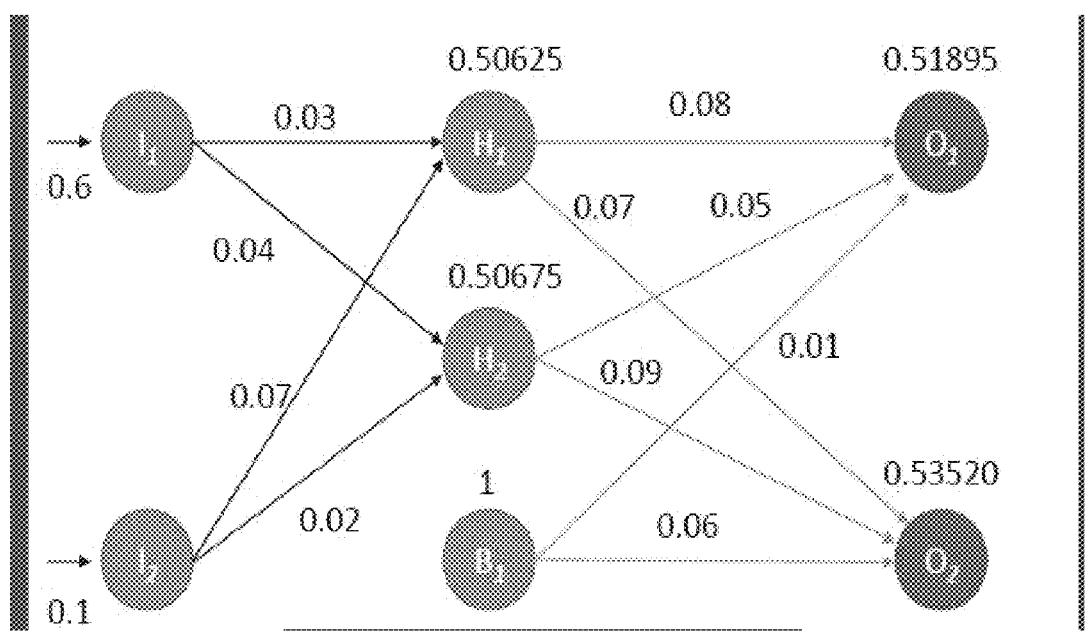
FIG. 17 is an illustration of exemplary computations of the NNM.

A NNM is a neural network architecture with a particular structure tailored to a particular problem statement. An exemplary problem statement the server's 114 neural networks model is the prediction of whether a given patient discharge from a particular facility is likely to suffer from preventable delay or not (in this example, a categorical output is predicted). Using a trained NNM, the server 114 predicts the likely outcome using a plurality of the properties or attributes of the pending patient discharge (the inputs). Each model in the system contains input, output, bias and hidden neurons. The input and output neurons are required whereas the bias and hidden neurons are optional depending on the nature of the specific problem statement and its requirements. Each model also has a structure. The exemplary neural network herein depicted in FIG. 17 is demonstrative of a feed forward structure, however other possible neural network structures or architectures include, but are not limited to ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), Radial Basis Function Network, Recurrent Self Organizing Map (RSOM), Self Organizing Map (Kohonen), among others. Feedback networks, for example Elman and Jordan Networks, are at times leveraged by the system particularly in instances where the sequence of events (order of data) is material. Each neural network model also has a defined activation function. In the exemplary neural network of FIG. 17, the activation function is the sigmoid function. Prior to model training, the model's neurons and their structure as well as the activation function are defined. The training of a model starts with the random selection of a set of initial synaptic weights. During the training process, the synaptic weights are updated after each training iteration (see further description provided herein). The below describes how the values at the neural network nodes $H_1$, $H_2$, $O_1$ and $O_2$ are calculated for given inputs $I_1$ and $I_2$ and a given set of synaptic weights (synaptic weight values for this example are those shown in FIG. 17). This calculation process is used during each model training iteration and subsequently when the trained model is used to make predictions from previously unseen input data:

$H_1$
Sum=0.6*0.03+0.1*0.07
=0.018+0.007
=0.025
Output=A(Sum)=0.50625

$H_2$
Sum=0.6*0.04+0.1*0.02
=0.024+0.002
=0.027
Output=A(Sum)=0.50675

$O_1$
Sum=0.50625*0.08+0.50675*0.05+1*0.01
=0.0405+0.0253375+0.01
=0.0758375
Output=A(Sum)=0.51895

$O_2$
Sum=0.50625*0.07+0.50675*0.09+1*0.06
=0.0354375+0.0456075+0.06
=0.141045
Output=A(Sum)=0.53520

During the training process, the synaptic weights are adjusted to minimize the error of the output. Thus, the final synaptic weights of the trained model are only known once model training is complete. After successful training of the model, the finalized synaptic weights are then used to make predictions.

Training the NNM

The server 114 applies machine learning algorithms to modify the synaptic weights of each model's connections as it learns the patterns in the data. Thus, trained models in the system are system models with finalized synaptic weights that result in the most minimal error. Training algorithms along with representative data sets presented to each of the models for the purpose of training are employed by the system to update the synaptic weights of each model's connections with values that minimize the error.

There are two types of error that pertain to neural networks. The first is Local Error (E). Local error is the actual output value computed by the neural network subtracted from the ideal value (i.e. the output value in the training data set). This error is "localized" to particular output neurons, hence the name local error. The other type of error is the error of the neural network, also called network error or global error. The global error is the cumulative effect of the error at each of the outputs (the local error for each output). There are a few types of global error which are briefly discussed below.

Mean Square Error (MSE)

$$\frac{\sum_n E^2}{n}$$

The mean square error (MSE) is the sum the square of all local errors divided by the total number of cases.

Sum of Square Errors (ESS)

$$\frac{\sum_n E^2}{2}$$

The sum of square errors (ESS) is the sum of the square of all local errors divided by two (2).

Root Mean Square Error (RMS)

$$\sqrt{\frac{\sum_n E^2}{n}}$$

The root mean square error (RMS) is the square root of the MSE.

The system generally uses MSE, however, in some specific instances the other methods for determining the global error are used.

To more formally state the objective of using machine learning to train the models in the system, it is most accurate to say that the system employs machine learning algorithms and training data to adjust the synaptic weights for the connections in each model such that the global error is less than a pre-established level. The system is configured with acceptable global error levels that balance the tradeoffs of model overtraining (acceptable global error level too low) and model undertraining (acceptable global error level too high).

Figure 18:
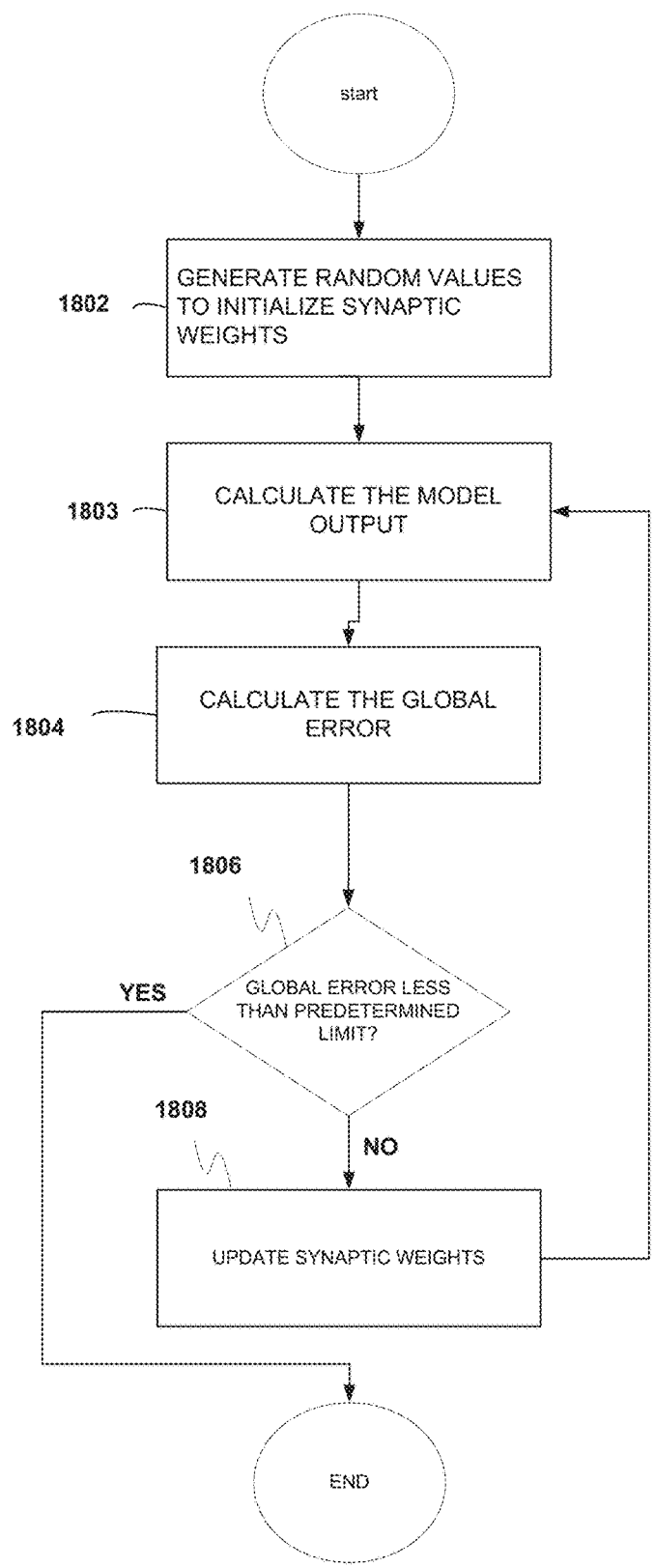
FIG. 18 is a flow diagram illustrating exemplary operations of the system for training the NNM.

Referring to FIG. 18, the approach for training the NNM based upon training data will be discussed. The training data is quantifiable outcomes (delayed or not delayed, delay time) of a plurality of past patient transactions and patient attributes of each of the past patient transactions. Initially, at 1802, values of the plurality of synaptic weights are assigned to random values. At 1803, the output values of the model are calculated for the current "row" or case in the training data being used for the current training iteration (i.e. "row" being the one transaction or case used for the current training iteration out of the available transactions in the training data set) using the initial random synaptic weights. At 1804, the global error for this iteration of the NNM training process is calculated. Particularly, a local error at each of the output(s) is calculated, which is the difference between each output value of the NNM on this iteration and the corresponding actual (known) quantifiable outcomes from the current "row" in the training data set. The global error is then calculated by summing all of the local errors in accordance with MSE, ESS and/or RMS discussed above. If it is determined that the global error is not less than a predetermined acceptable global error (NO at 1806), the values of the synaptic weights are adjusted at 1808, and a new training iteration using another patient transaction from the training data set begins (at 1803). As part of this next iteration, the global error is again calculated at 1804. Here, if the global error is never reached after a number of iterations, the model can be revised, such as changing the number of hidden layers, neurons, etc., and the training process can be attempted again. When it is determined that the global error is less than the predetermined acceptable global error (YES at 1806), the trained model is then subjected to validation discussed later.

Different machine learning algorithms as well as different global error calculation methods can be employed to update the synaptic weights. Some of the machine learning algorithms the server can be configured to employ include ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), among others. Machine learning algorithm selection is determined based on a number of factors some of which include accuracy of the algorithm, the computation resources available and those required of the algorithm, the available or ideal training time duration, among others.

Figure 19:
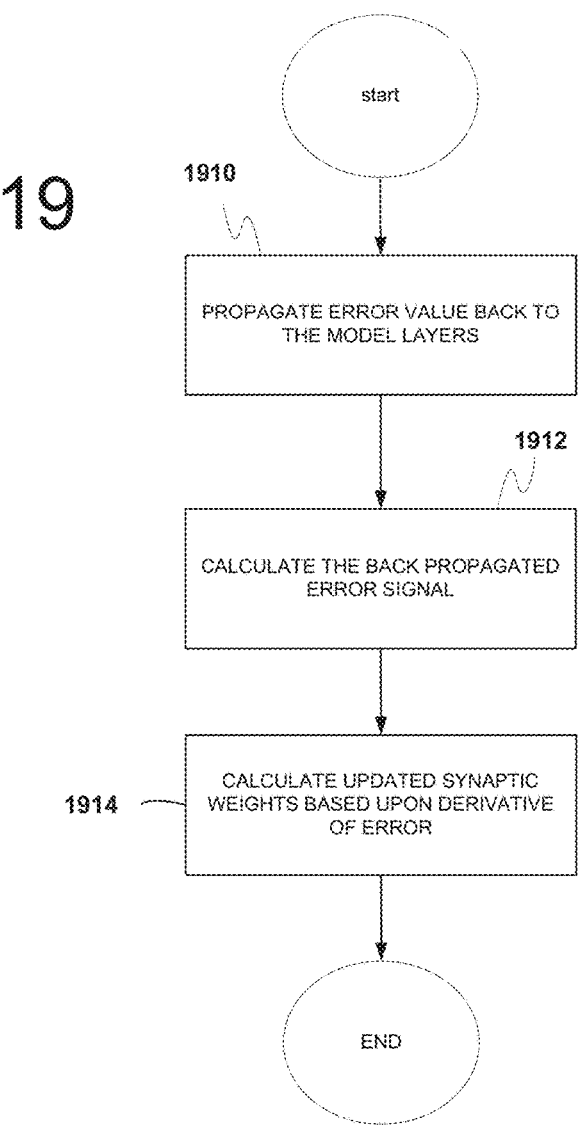
FIG. 19 is a flow diagram illustrating exemplary operations of the system for propagation training (updating the synaptic weights between iterations) of the NNM.

Training the system models is an iterative process referred to as propagation. As discussed above, the process begins by using randomly assigned synaptic connection weights to compute the outcome of the model (1803). Using the known output values for cases in the training data set and the output values computed by the model, the local error at each output, and subsequently the global error of the network is determined (1804). If the global error is not below the pre-established acceptable global error rate a new iteration with updated synaptic weights will ensue. The process for updating the synaptic weights (1808) is referred to as propagation training. As already discussed, the system can be configured to employ one of a variety of methods (algorithms) for updating the synaptic weights during the training process for a given model. Referring to FIG. 19, a gradient-decent procedure can be used to update the synaptic weights on each training iteration. At 1910, the error value is propagated to the model layers. The gradient-decent procedure is used to determine the direction of change of the synaptic weight(s) that will minimize error on the next iteration. Doing this requires model neurons to use differentiable activation functions, such as those already previously discussed herein. At 1912, the back propagated error signal is determined by calculating the error gradient (gradient-decent procedure). The error gradient is the value of the instantaneous slope at the current point on the error function surface plot. Said another way, the error gradient is the derivative value of the error function surface plot, the plot of the error values that correspond to different synaptic weights. The proportion of the error gradient that is used in each iteration of the propagation process is called the learning rate and can be configured in the system (essentially, how much of the derivative value should be applied to update the synaptic weights on each model training iteration). This procedure can vary depending on the propagation algorithm employed by a given model in the system. The larger the learning rate, the larger the synaptic weight changes will be on each iteration and the faster the model will learn. However, if the learning rate is too large, then the changes in the synaptic weights will no longer approximate a gradient decent procedure (a true gradient decent is predicated on infinitesimal steps) and oscillation of the synaptic weights can result (no learning at all). Conversely if the learning rate is too slow, training of the model will be a very lengthy process utilizing large amounts of compute time. The learning rate that is used for training the system models is one that results in brisk learning without triggering oscillation. When the system is configured with optimal learning rates the fastest training of each model is achieved with the smallest compute training time expenditure.

The model propagation training process utilized by the system can also employ the concept of momentum to deal with the challenge of local minima that can complicate backpropagation (the process of following the contour of the error surface with synaptic weight updates moving in the direction of steepest decent), for example, when the network architecture includes a hidden layer. Momentum is the concept that previous changes in the weights should influence the current direction of movement in the weight space (essentially the percentage of previous iteration weight change to be applied to the current iteration). As such, the inclusion of the momentum parameter can help networks employed by the inventive system to "roll past" local minima. In addition, the inclusion of the momentum parameter can also help speed learning, particularly when long flat error surfaces are encountered. At 1914, the updated synaptic weights are calculated based upon the derivative of the error, the defined learning rate and the momentum parameter.

Training and Validation of System Models

Figure 20:
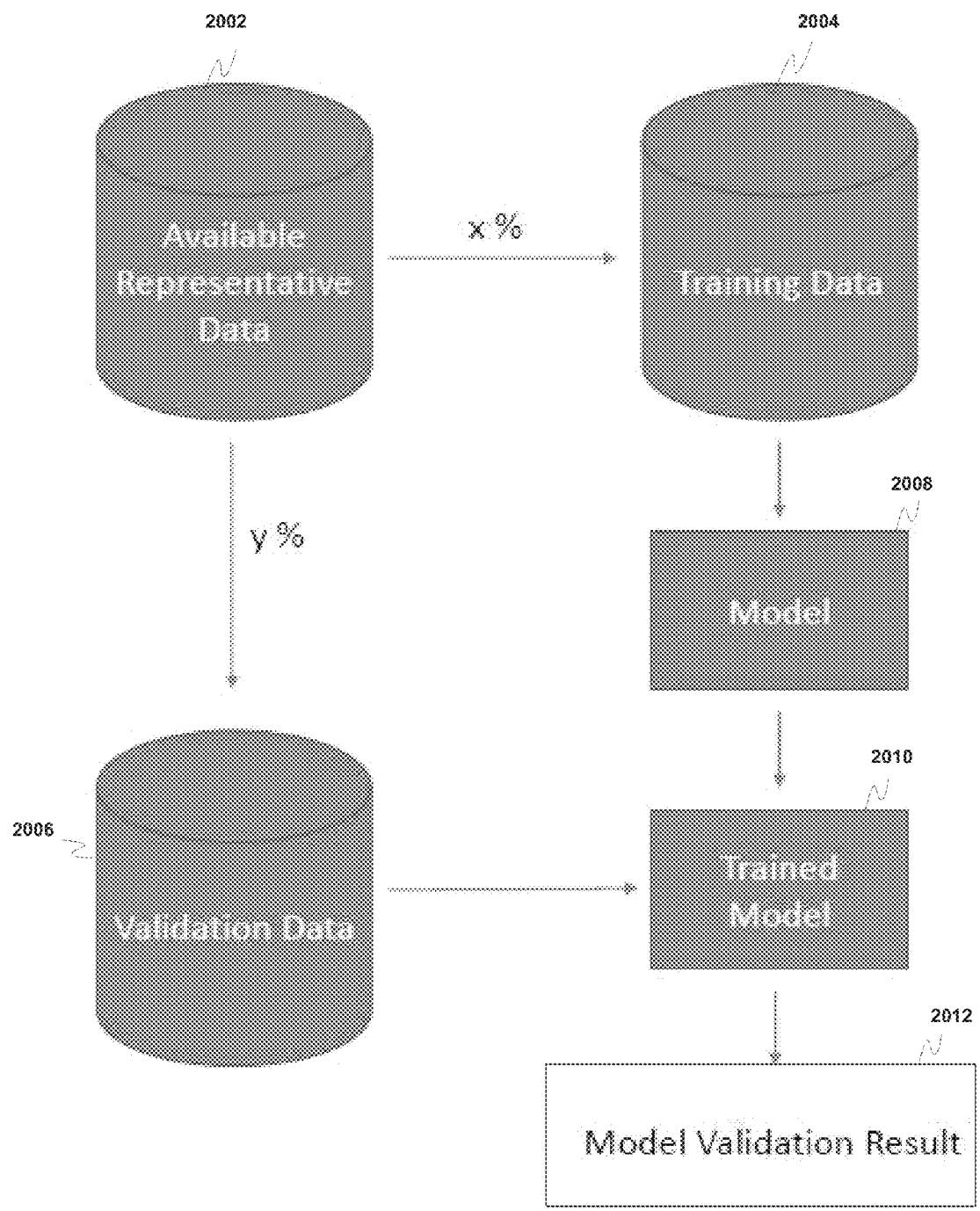
FIG. 20 is block diagram illustrating high level operations of the process for training the NNM and validating the trained NNM.

The training process for the NNM employs a representative data set, which can be a plurality of past patient transactions as discussed above. Referring to FIG. 20, the cases in the representative data set 2002 are divided into two unique data sets by some ratio or percent x allocated to the training data set 2004 and percent y allocated to the validation data set 2006. The ratio of cases allocated to the training data set 2004 versus those allocated to the validation data set 2006 varies. Before the allocation of cases to the training data set 2004 or the validation data set 2006, an optional step of data shuffling can be carried out by the system to help ensure all types of data in the representative data set 2002 gets distributed to both the training 2004 and the validation 2006 data sets. The training data set 2004 was used to train the NNM 2008 as discussed above. The validation data set 2006 can be used to validate the trained NNM 2010 because the real outcome of each case in the validation data set is known. The server can generate an output value (model validation result) 2012 of the trained NNM 2010 for each past patient transaction of the validation data set 2006, wherein each of the output values 2012 represents a calculated quantifiable outcome of the respective patient transaction. Then the server can determine if the output values 2012 correspond to the quantifiable outcome within the predetermined global error.

The training data set 2004 along with the defined system models, the selected machine learning training algorithms and the method each uses for global error calculations, in conjunction with the pre-defined acceptable global error rates are used to train the NNM starting with randomly assigned synaptic weights for each model's neuronal connections. The requisite number of synaptic weight calculation iterations are executed until an acceptable global error level is obtained. Subsequently, the trained model 2010 is then used to predict the outcome for cases in the validation data set 2006, the so called "unseen data" (from the perspective of the trained model). Because the real outcome of each case in the validation data set is known, at this point a validation report can be generated comparing the predicted results with the actual results and the findings can be used to determine the validity of the trained model, essentially whether it is successfully predicting the actual outcomes for the cases in the validation data set. The end result is an assessment of how well the trained system model performs on unseen data.

Using the Trained NNM

Returning to FIG. 11A, the backend device receives a plurality of input attributes of a new patient transaction. This data may come from a client device, from the database at the server, or a combination. The data is pre-processed (for example, normalized) to generate an input data set, and the data is input into the trained model 1107 which then generates an output value. The output value is then post-processed (for example, de-normalized). Finally, the output value is classified into a delay risk category (classification task) or a value such as the probability of delay or the predicted duration of delay (regression task) to predict the outcome. For example, in the simplest case the de-normalized output value can be a Boolean value (delayed or not delayed). In another case, the output value can be a probability of delay occurring. In this case, the TMD or server may assign probability ranges which define particular delay categories. In another case, the output value can be a calculated delay time (predicted duration of delay). In this case, the TMD or server may assign time ranges define particular delay categories.

Unsupervised Learning

Figure 21B:
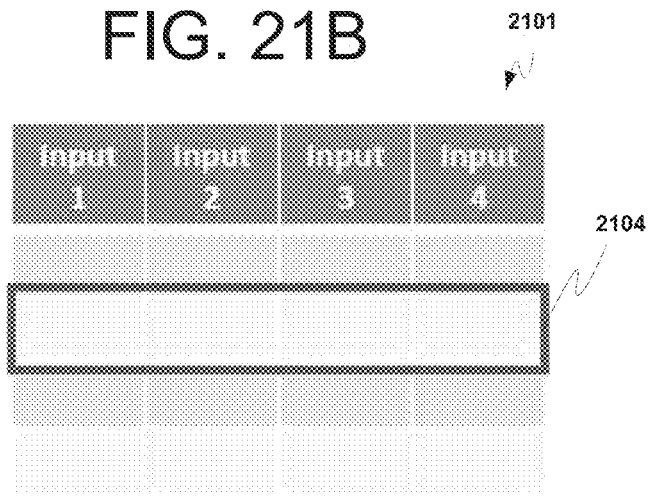
FIGS. 21A-21B is an illustration of an exemplary Self-Organizing Map (SOM) and the input data set to the SOM network.
Figure 21A:
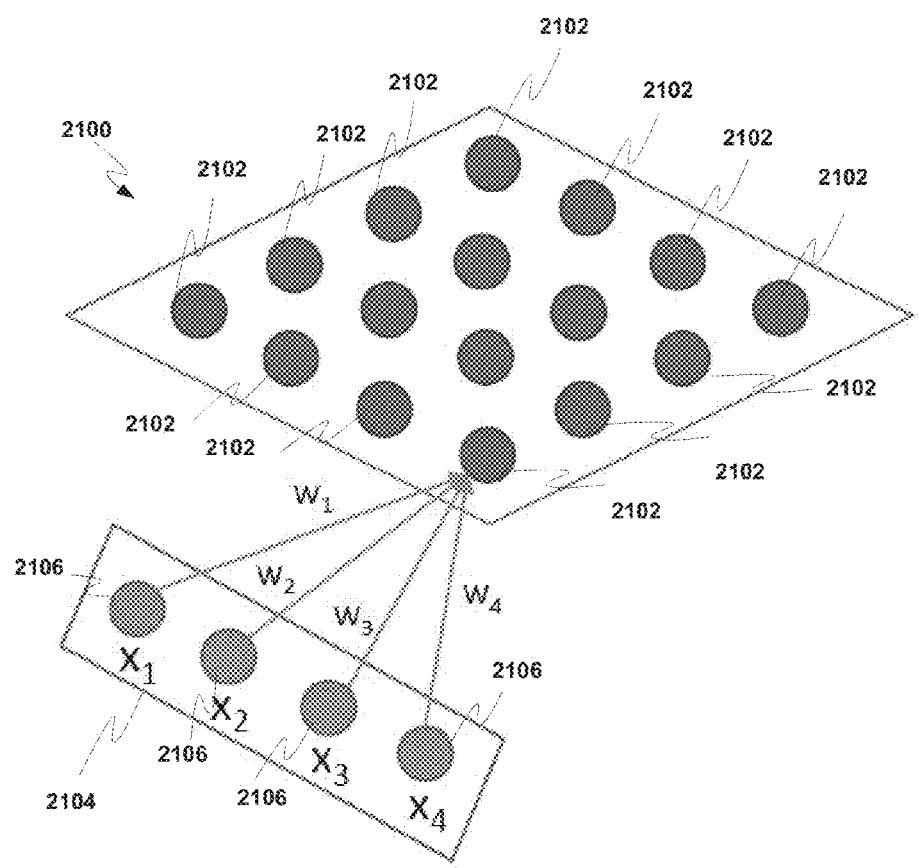
Figure 21C:
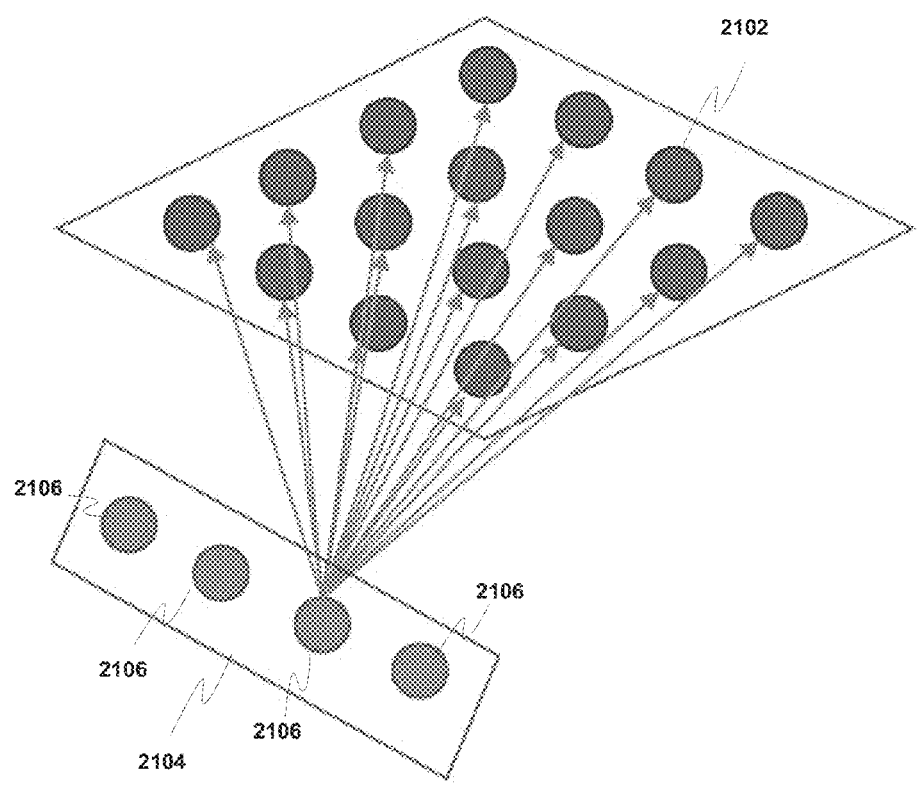
FIG. 21C is an illustration of how each node of the SOM network will contain the connection weights of the connections to all connected input nodes.

The server can also use unsupervised learning techniques as well as supervised learning techniques to determine the group or cluster to which particular patient transactions belong. Referring to FIGS. 21A-21B, a Self-Organizing Map (SOM) 2100 is an unsupervised neural network that consists of a grid or lattice of nodes 2102 with a certain structure which may be one, two or three dimensional. The SOM 2100 includes a grid of nodes 2102 on some two (or three) dimensional plane where each node has an x and y coordinate (and z coordinate in the case of a three-dimensional node network), a so called fixed topological position, and an input layer 2104 with various input nodes 2106 that are used to provide input to the SOM network 2100. The input layer 2104 can be a random row from the training data set 2101 (FIG. 21B). The specific number of inputs is dependent on the specifics of the data set. Each input node is connected to every node of the two (or three) dimensional SOM network (FIG. 21C) and each connection has a synaptic connection weight (w), much like that in supervised networks. Each node 2102 of the SOM network 2100 will contain the connection weights of the connections to all connected input nodes. As partially shown in FIG. 21C, each SOM network node 2102 is connected to all input nodes 2106, thus each node of the SOM network will have an equivalent number of connection weights (equivalent to the number of input nodes).

Figure 22:
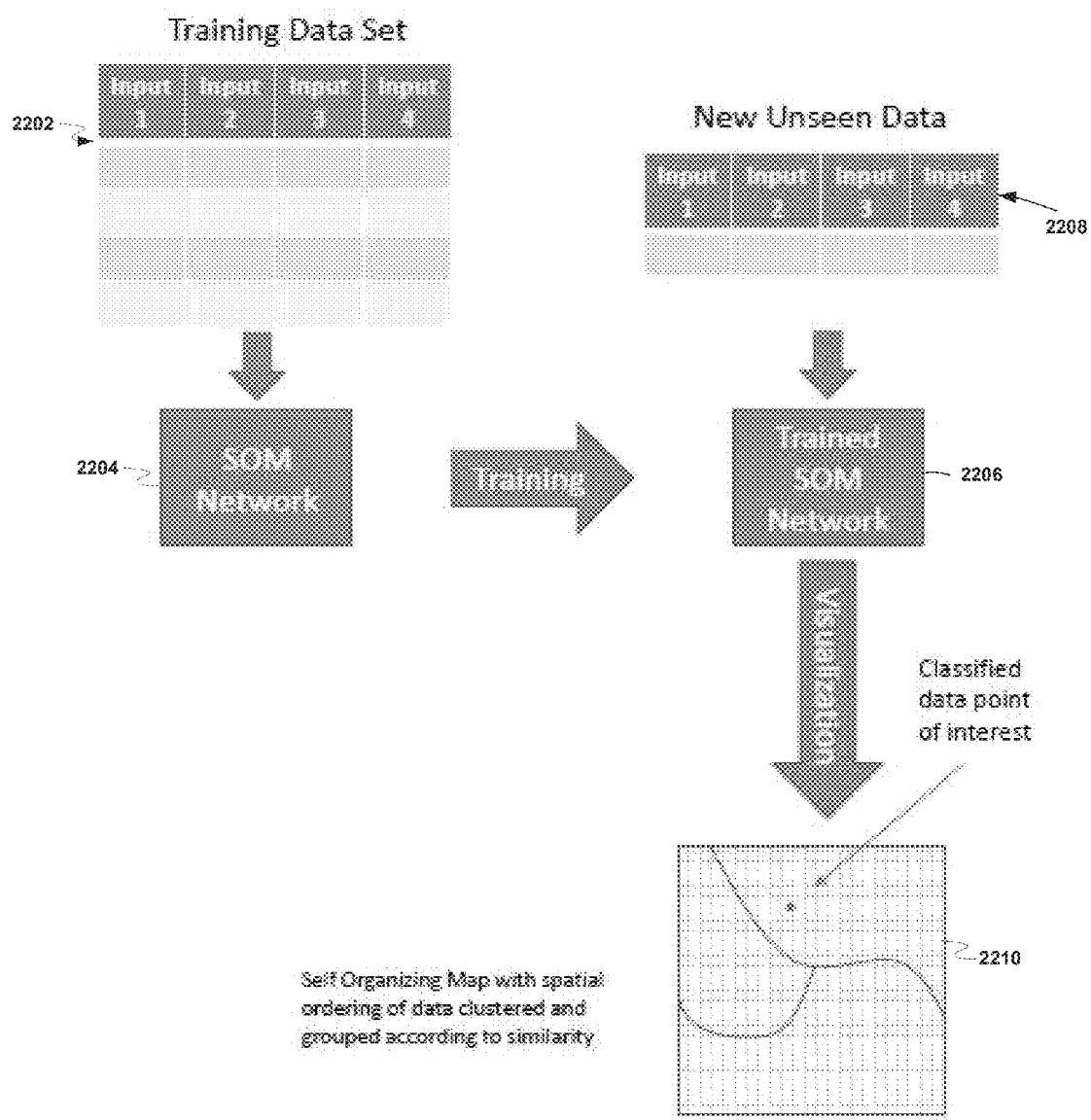
FIG. 22 is a block diagram illustrating high level operations of the process for training the SOM.

A representation of the process for creating, training and using the trained model is shown in FIG. 22. A training data set includes a plurality of patient attributes of past patient transactions. The training data set 2202 is input into the SOM network 2204. The SOM network 2204 is trained to generate the trained SOM network 2206. New data 2208 is input into the trained SOM network 2206. The output of the trained SOM network can be an SOM image 2210 that shows spatial ordering of data clustered and grouped according to similarity such that that the group or cluster to which a given data point of interest belongs can be determined. As discussed later, the SOM image 2210 can be rendered on a client device.

Figure 23:
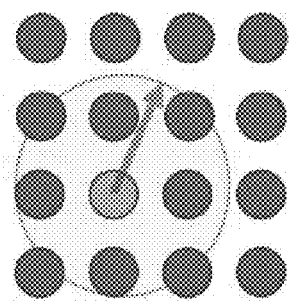
FIG. 23 is an illustration of the process for training the SOM network.

Referring to FIG. 23, the first step in SOM model training is to initialize values of the plurality of synaptic connection weights to random values. The next step is to randomly select one row (one past patient transaction) from the training data set, which is most typically normalized (for this purpose) and determine which of the plurality of network nodes is the best matching unit (BMU) according to a discriminant function such as a Euclidean Distance. When a node is selected and compared with the row selected from the training data, the Euclidean Distance which serves as our discriminant function for this competitive network, is calculated, though others, for example, Manhattan distance, can be used. This process is repeated for each SOM node. The SOM node with the smallest Euclidean distance (or said another way, the neuron whose weight vector comes closes to the input vector) will be designated as the BMU for that randomly picked input data row. Thus, the BMU is the closest SOM network node to the randomly picked input data row. Next, the neighborhood radius, or the so called neighborhood kernel (function), is calculated. Usually the Gaussian function is used, although the Bubble function is another possibility. The neighborhood radius allows for the determination of the specific BMU neighborhood nodes in the SOM network to which connection weight updates should be applied on the next training iteration. All nodes within the "circle of influence" corresponding to the neighborhood radius are updated. The procedure used to calculate this radius value is shown below:

$$r(n) = r_0 e^{-\left(\frac{n}{\lambda}\right)}$$

$r_0$=initial radius
n=iteration number
$\lambda$=time constant

Usually a large initial radius value is selected for the purpose of having the almost the entire network covered. n is the iteration number and lambda is a time constant (iteration limit). This calculation of the radius is basically a decreasing function whereby the value of r will diminish over the course of the training iterations, another way of saying the topological neighborhood decays with distance or that the topological neighborhood decreases monotonically over the period of iterations. Hence a greater number of SOM nodes are updated early in the training process, and on subsequent rounds there is a smaller number of nodes in the neighborhood of the BMU that get updated. At this point in the training process the connection weights are updated for the BMU and those nodes in the neighborhood of influence. The connection weight update equation is as follows:

$$W_k(n+1)=W_k(n)+\alpha(n)h_{ck}(n)[x(n)-W_k(n)]$$

Where n is the iteration number, k is the index of the node in the SOM network, and $W_k(n+1)$, is the updated connection weight (weight vector of node k) for the next training iteration which is calculated as shown using $\alpha(n)$, a monotonically decreasing learning coefficient (learning rate), $h_{ck}(n)$, the neighborhood kernel (function)—something that, for simplicity can be called the influence factor, and $[x(n)-W_k(n)]$, the difference between $W_k(n)$, the old weights (the weights on the current training iteration), and $x(n)$, a randomly selected row or input pattern from the input data that was used on the current iteration.

Thus, a simplistic way of stating this is the new weights for the next training iteration are calculated by adding the old weights from the current training iteration to the product of the learning rate multiplied by the influence factor multiplied by the difference or delta between the old weights and the randomly picked input data used for a given training iteration. Note the influence factor is often a radial based function such as the Gaussian function (though as mentioned earlier, other types of radial functions can also be used) and this is the reason why the nodes closest to the BMU have or receive more influence than those further away from the BMU which are updated by a smaller amount. Also, in regards to the learning rate, it decreases (decays) over time, meaning that in the earlier phases of the training process, there is more learning, but over the training period the learning effect will decrease in each sequential iteration. The delta between the old weights and the randomly picked input data used in a given training iteration is a determinant of how different the current SOM network node is in comparison with the randomly picked input data row used on the given training iteration. Hence, these three factors are the determinants of the updated connection weights that should be used on each subsequent training iteration for the SOM network nodes. So the learning rate and the influence factor decay over the period of iteration to allow for the proper convergence of the solution such that a stable result can be obtained at the end of training. The training process is repeated for a fixed number of N iterations to generate the trained SOM network.

Figure 21D:
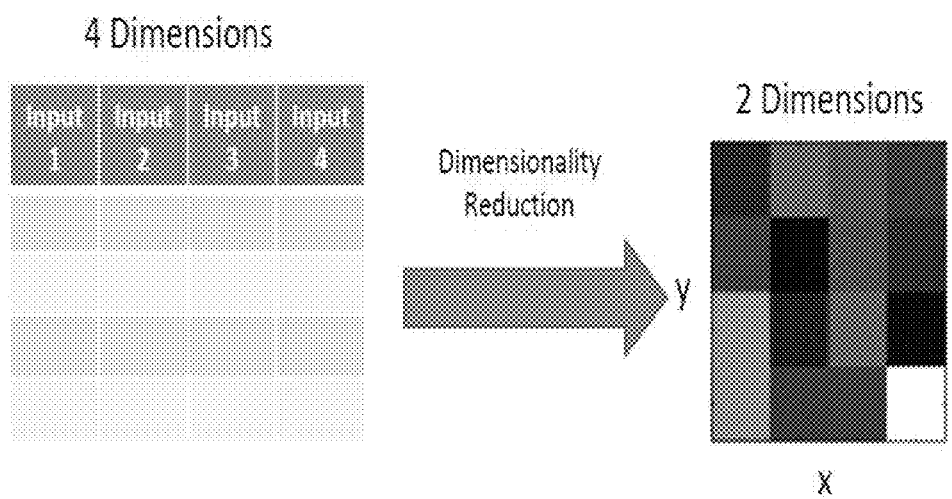
FIG. 21D is an illustration of the SOM network used to reduce dimensionality of the input data sets.

Referring to FIG. 11B, an exemplary data set includes a plurality of data [1, 2 . . . N], and a number of properties [1, 2 . . . N] for each data. The data set can be a plurality of past patient transactions and the properties can be a number of attributes of each past patient transaction. The high dimensionality of the data sets can make visualization of the data difficult. As illustrated in FIG. 21D, the dimensionality reduction aspect of SOM networks allows data of high dimensionality to be projected to a two-dimensional grid which expresses the similarity of samples and the distance between them. However, the mere position on the map cannot sufficiently embody the complexity of an n-dimensional vector. The challenge of information representation is a mature area of research and numerous approaches of displaying multidimensional multivariate data have been proposed as discussed in the article entitled "30 Years of Multidimensional Multivariate Visualization" authored by Wong and Bergeron (1997), the contents of which are hereby incorporated by reference. One such technique therein described utilized by the system is Scalable Vector Graphics (SVG), an XML markup language for describing two-dimensional vector graphics, both static and animated.

Figure 24:
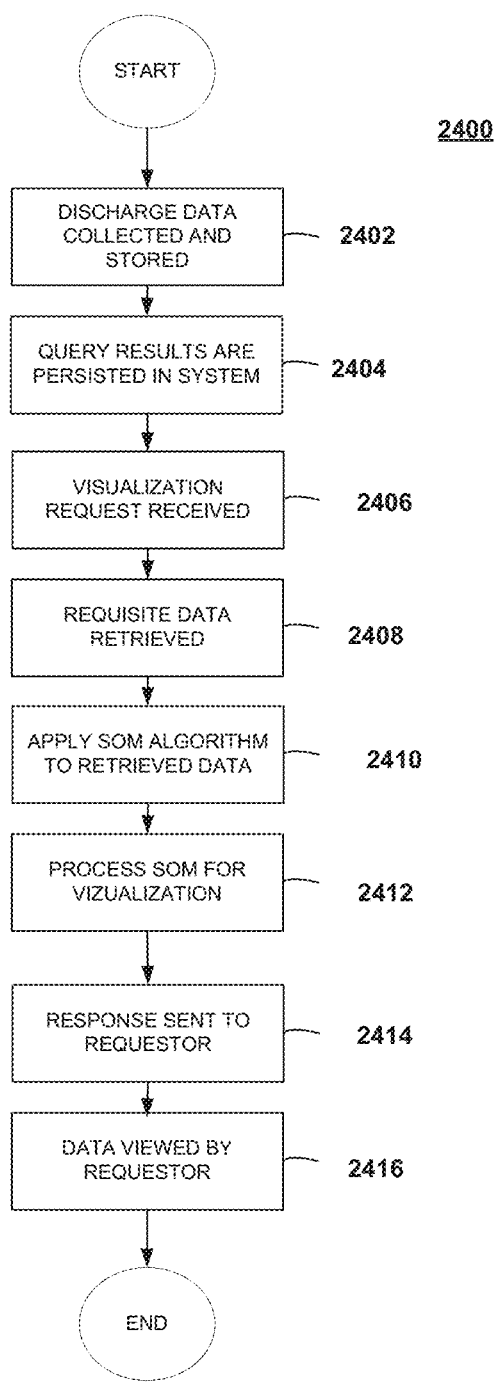
FIG. 24 is a flow diagram illustrating exemplary operations of the system to generate the graphical image including the visualization.

Referring to FIG. 24, an exemplary process 2400 by which the system can employ SOM network to take a data set of discharges defined by n-dimensional input attributes and generate a visualization of the results after passing the data into a SOM network will be discussed. At 2402, discharge data is collected and stored. Particularly, the DCE collects location data on the patient from the RFID tags as discussed above and transmits it to the backend devices. This data can be stored in the database at the server with respect to the patient as discussed above. At 2404, the server (or TMD) can maintain query results in the memory. At 2406, the TMD receives a visualization request from a client device or web browser via the network with query parameters. At 2408, the TMD sends a data request with the query parameters to the server, which retrieves from the database the data sets consistent with the request. At 2410, the server inputs the data sets to the trained SOM network. At 2412, the server generates a visualization or graphical image based upon the output from the SOM network. At 2414, the server sends the graphical image to the TMD, which either sends it to the client device and/or renders the image on a display of a website. The output produced can be groupings or clustering of discharges with similar characteristics, much like the classical "market segmentation" or "document classification" tasks for which SOMs are widely employed. This SOM output can be generated from a variety of vantage points or perspectives with one or more specified criteria, for example, specific time ranges, or for only delayed discharges, or only for a particular subset of discharges processed by a particular employee, a group of employees, a service line, a group of service lines, a hospital facility or a group of hospital facilities in a given region, to name a few examples. SOM techniques can also be employed to predict the classification, type, or grouping of a particular pending hospital discharge leveraging the attributes or inputs from an already existing data set of discharges, for example.

Exemplary Implementation

An exemplary implementation will be discussed for a case in which a NNM is created, trained and validated to determine whether a given patient discharge is likely to be delayed. This example was selected for its simplicity and the inputs were crafted to be of a flavor that is easily understood by a human, while also still being demonstrative of the inventive system's capabilities. The example is not intended to denote or to imply any limitation to the scope of attributes consumed as inputs by the system nor the scope or extent of the system's outputs and its ability to predict these outputs. While in practice the models will be more complicated, the embodiment herein is demonstrative of the modeling process (the process of developing the neural network architecture) utilized in the inventive system. The example of the model's implementation, training, and validation is provided utilizing the c# programming language (Microsoft) and an open source machine learning library (Encog). However, the neural network models can be implemented in any variety of computer languages or logic and can be trained utilizing appropriately selected machine learning training algorithms as implemented in a variety of 3$^{rd}$ party libraries or in-house proprietary code. The exemplary embodiment herein is a simple feed forward neural network.

The backend devices (TMD and server) can be employed by healthcare systems to predict the likelihood of discharge delays. For example, the database at the server device can store historical discharge data from a hospital. Each of these historical discharges provide input data, specifically an attribute about the patient, an attribute about the patient's attending physician (MD), an attribute about the patient's assigned nurse, and an output, namely whether the discharge was significantly delayed or not. In this simple example, the patient attribute is the presence of polypharmacy. For this example, we will define polypharmacy as more than 20 discharge medications. The admitting attending physician attribute is whether or not the attending physician is also the patient's outpatient primary care provider (PCP). Finally, the nurse attribute in the input data set is also a binary input, specifically whether or not the nurse (RN) assigned to the care of the patient at the time of discharge is an experienced nurse (i.e. not a new hire, where a new hire is defined as a newly minted nursing school graduate—just earned his or her Bachelors of Science Degree in nursing within the last 6 months—who is a new hire to the healthcare system in their current role for less than 4 weeks). The existing data set available is that shown in the table below where the number 1 denotes the presence of the attribute and 0 denotes the absence of the attribute.

| Input 1: + Polypharmacy | Input 2: + Admitting MD is PCP | Input 3: + Patient's assigned RN is experienced | Output: + Discharge Significantly Delayed |
|---|---|---|---|
| 1 | 1 | 0 | 0 |
| 1 | 0 | 1 | 0 |
| 1 | 1 | 1 | 0 |
| 1 | 0 | 0 | 1 |
| 0 | 0 | 0 | 0 |
| 0 | 0 | 1 | 0 |
| 0 | 1 | 0 | 0 |
| 0 | 1 | 1 | 0 |

As shown below, the input data set training data and the output data from the above table is next put into an array of double arrays. One is created for the input data and one is created for the output data.

```
namespace _006_1.ExemplaryEmbodiment
{
  class Program
  {
    static void Main(string[ ] args)
    {
      double[ ][ ] exemplaryEmbodimentInput =
      {
        new[ ] {1.0, 1.0, 0.0},
        new[ ] {1.0, 0.0, 1.1},
        new[ ] {1.0, 1.0, 1.0},
        new[ ] {1.0, 0.0, 0.0},
        new[ ] {0.0, 0.0, 0.0},
        new[ ] {0.0, 0.0, 1.0},
        new[ ] {0.0, 1.0, 0.0},
        new[ ] {0.0, 1.0, 1.0}
      };
      double[ ][ ] exemplaryEmbodimentOutput =
      {
        new [ ]{0.0),
        new [ ]{0.0),
        new [ ]{0.0),
```
-continued
```
        new [ ]{1.0),
        new [ ]{0.0),
        new [ ]{0.0),
        new [ ]{0.0),
        new [ ]{0.0)
      };
```

The crux of any application of machine learning is development of an appropriate model for the problem that needs to be solved. as shown below, for the simplistic example, a simple feed forward neural network is used. The neural network includes an input layer with three input nodes in the input layer, a hidden layer and an output layer. For each input neuron, no activation function is specified (note null value); alternatively a linear activation function could have been employed instead, as a linear activation function simply would mirror the input. A hidden layer is also specified for the model, containing three neurons as well as bias neuronal input. For each hidden layer neuron, the Sigmoid activation function is specified. Finally, for the current problem, one output neuron is required in the output network layer. No bias neuronal input is included, and again the Sigmoid activation function is specified. Once the networks neuronal layer architecture has been defined, the network is finalized and the synaptic weights are initialized to random values.

```
private static BasicNetwork Create Network( )
{
  var network=new BasicNetwork( )
  // input layer, 3 neurons, with bias neuron, no activation fxn
  network.AddLayer(new BasicLayer(null, true, 3));
  // hidden layer, 3 neurons, with bias neuron, sigmoid activation fxn
  network.AddLayer(new BasicLayer(new ActivationSigmoid( ), true, 3));
  // output layer, 1 neuron, no bias neuron, sigmoid activation fxn
  network.AddLayer(new BasicLayer(new ActivationSigmoid( ), false, 1));
  network.Structure.FinalizeStructure( );
  // randomly initialize network synaptic weights
  network.Reset( );
  return network;
}
var network=Create Network( );
```

RGiven the neuronal architecture is now finalized, the model is ready for training. For this exemplary embodiment a first order resilient propagation (RProp) supervised learning algorithm, is utilized to train the model. The training data set is passed into the neural network which has been configured with the RProp training algorithm.

```
var trainingSet=new BasicMLDataSet(exemplaryEmbodimentInput, exemplaryEmbodimentOutput);
// training algorithm that will be used to train the network
var train=new ResilientPropagation(network, trainingSet);
```

A predefined acceptable global error value of global error less than or equal to 0.001 has been decided upon and is used as the training iteration terminating condition for the do while loop. Multiple training iterations are executed and the global error at the end of each iteration is determined and assessed to see if it meets the established terminating condition. If an acceptable global error level has not yet been achieved, the synaptic weights for each interneuron connection in the network will be subsequently adjusted and another training iteration then ensues. This process is continued until the updated synaptic weights in a given training iteration yield an output with global error less than the predefined condition. Once this terminating condition is met, the end result is the trained model.

```
// TRAIN THE MODEL
var epoch=1;
do
{
   // initiated training iteration
   train.Iteration( );
   // write iteration number and training error to console
   Console.WriteLine("Iteration No {0}: \tError: {1}",
epoch, train.Error);
   // epoch will increase by 1 in each iteration
   epoch++;
   // check value of training error at end of each iteration (terminating
      condition)
   // predefined limit value set to 0.001
} while (train.Error>0.001);
```

Figure 25A:
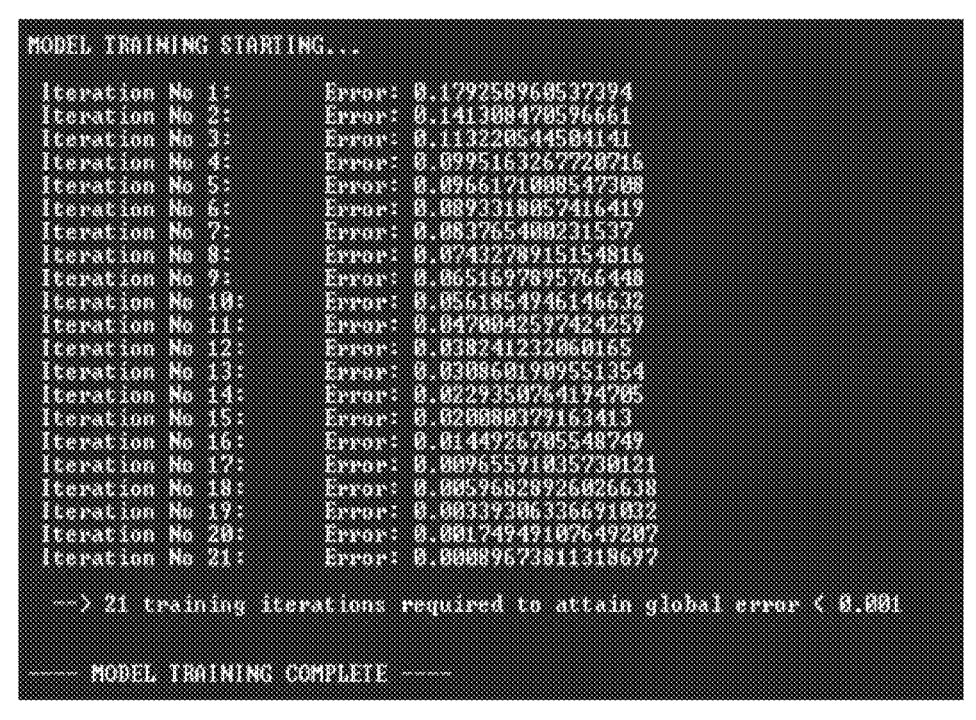

Referring to FIG. 25A, the output of each training iteration in this demonstrative example is shown. A total of 21 training iterations were required before an acceptable global error level was attained.

Now that the exemplary neural network model is trained and "learned," it is ready to undergo validation. For the purpose of this exemplary embodiment, the training data is passed into the trained model to assess its performance.

```
// EVALUATE THE MODEL
// in this simplistic exemplary embodiment we pass the model the training data
//set again
foreach (var item in trainingSet)
{
   // pass in row in data set
   var output=network.Compute(item.Input);
   // write output to console
   Console.WriteLine(
   "Input: {0:0.0}, {1:0.0}, {2:0.0}"+
   "\tIdeal: {3:0.0}"+
   "\tPredicted: {4}",
      item.Input[0],
      item.Input[1],
      item.Input[2],
      item.Ideal[0],
      output[0]);
}
```

The trained model's performance with this training data set are shown in FIG. 25B. For each input, the trained model's predicted output nicely approximates the ideal output providing evidence that the model is performant at predicting the outcome in all presented cases.

Figure 28:
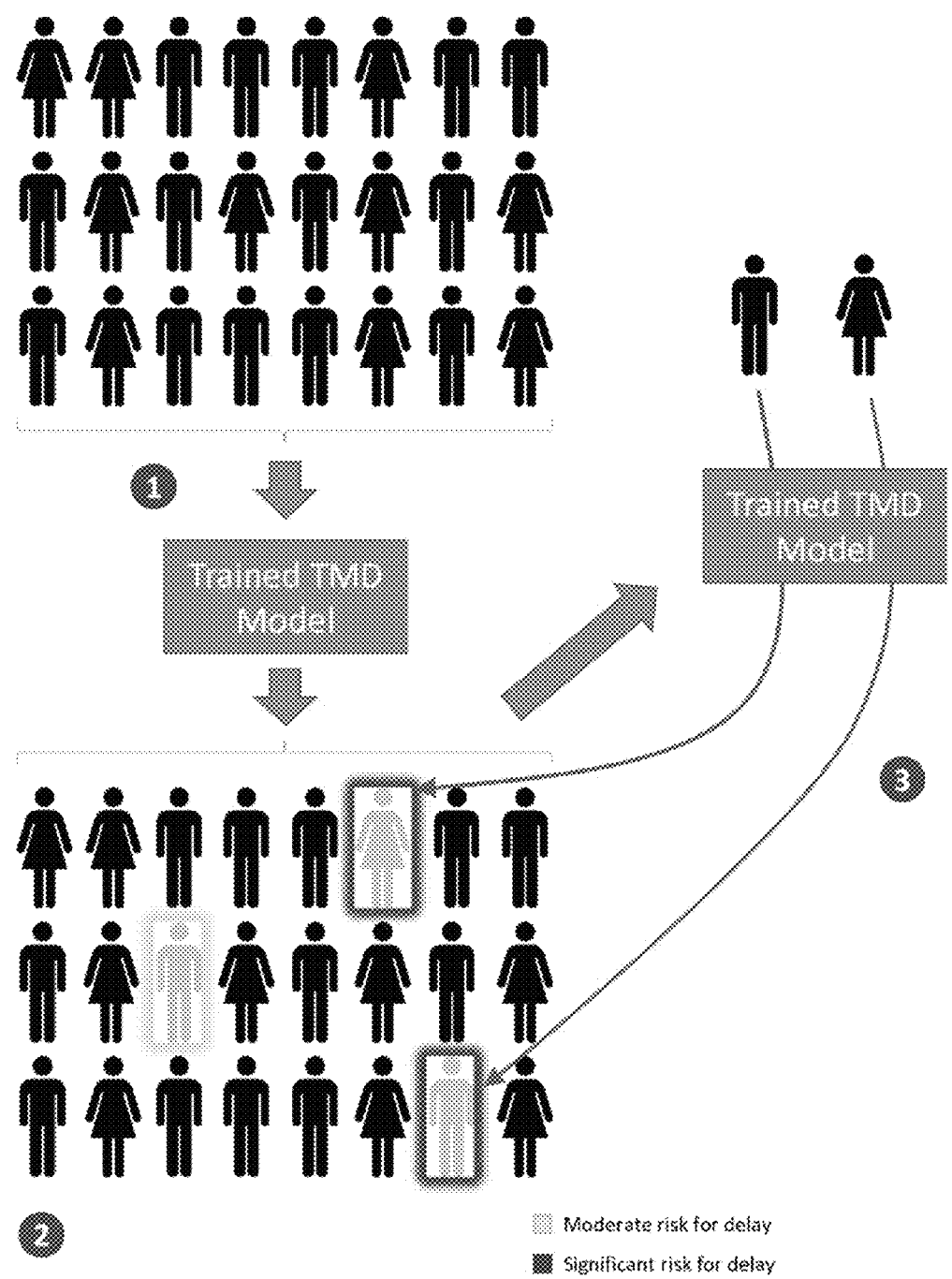
FIG. 28 is an illustration of an exemplary use case in which the trained TMD device determines a delay risk for a plurality of patient transactions and to which of the patient transactions resources should be deployed.

Referring to FIG. 28, the backend devices (TMD and server) use NNMs to predict which transactions are at risk for delay (i.e. which patient discharges for which orders have been written are at risk for delay) as described elsewhere herein. In addition, as illustrated in FIG. 28, the backend devices are capable of using their NNMs to determine to which, if any, transactions more resources should be allocated (i.e. the backend devices can determine whether there is an opportunity, or more specifically, a high probability, of successfully mitigating the likelihood of a given predicted discharge delay by allocating additional resource(s)). Particularly, to do this, the controller of the TMD may utilize a NNM that takes inputs such as delay risk category (moderate or significant risk for delay) of the patient transaction, attributes of the patient and the patient's hospital stay, the service line the patient is on, attributes of available clinical resources (for example, the available help resources' expertise and past performance on discharges with similar patients or discharges with similar attributes), etc.

In doing so, the TMD can determine whether (the probability that) deployment of any given available resource(s) is likely to mitigate the predicted discharge delay for a given patient discharge transaction that is pending fulfillment; moreover, the TMD's NNMs can predict the quantity or duration of time by which the delay would potentially be reduced if a given resource allocation recommendation is made. Based on business logic and these results, the TMD may determine it does or does not recommend that any of the available additional resources be deployed. There are a number of approaches the TMD could take to arrive at a decision to recommend or not recommend the deployment of any available resource(s). One demonstrative approach the TMD might take would be to recommend the deployment of an available resource if the probability weighted reduction in the duration of the predicted delay exceeded a particular threshold. If more than one potential allocation of available resources might be feasible at any given time, the business logic of the TMD, for example, could be configured such that the TMD issues the recommendation that in the net (summed together) results in the largest probability weighted delay reduction for the hospital system as a whole at that moment—i.e. the constellation of recommendations at that moment that collectively has the maximum potential beneficial impact (probability weighted delay duration reduction) for the hospital in question. Those skilled in the art know there is a broad set of approaches that the system may take to make such recommendations and the approaches can further vary depending on the specific optimization objective(s). Moreover, while in practice the optimization technique employed may be more complex, the embodiment herein was selected to provide a simple demonstrative example of one of many potential optimization approaches the system might take. The resource allocation example herein is not intended to limit the scope of potential approaches to that described.

Figure 29:
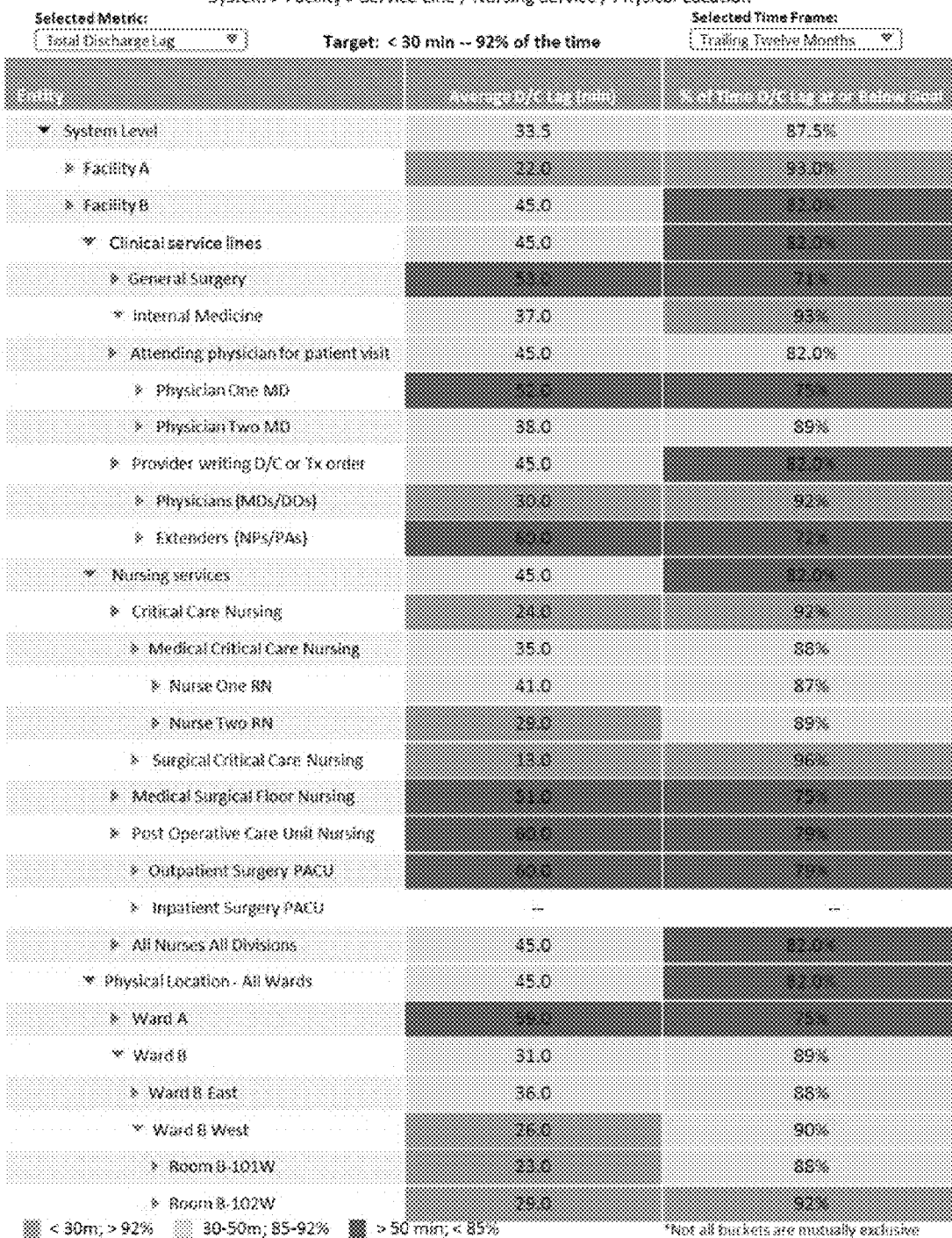
FIG. 29 is an illustration of an exemplary system level discharge performance graphical display.

Referring to FIG. 29, the system provides a user interface users can use or alternatively the user can author code for a client that will directly communicate with an application programming interface (API) exposed by the backend devices with access regulated via the use of a security token and/or an API key that references the developer's organization to configure particular metrics (related to the relationships and events the system captures) that they desire to follow and measure over time and in real time. Each metric can also be associated with an icon (not shown) and the user can configure particular colors for the icon (not shown) or a cell where a given metric value is displayed (shown) that would correspond to particular values of or value ranges for the respective performance metric. The end user can configure one or more target levels of performance for each metric that may or may not correspond with some description of the level of performance. The system allows end users to provide meta-data about the performance metric as well (i.e. descriptive attributes about the performance metrics).

The system can be integrated into third party clinician/healthcare provider/patient facing applications running on a client device. The client applications may incorporate icons with our without categorical color designations or data tables with or without color encoded cells to communicate information about a given metric or concept. Business logic for the display color can be utilized by the client application on any given client device. The icons (not shown) or data tables with metric values (shown) can appear in the client application in association with various combinations of healthcare providers, patients, patient visits, patient facility visits, patient provider encounters, etc. The colored icon and/or color encoded data table can appear in various areas of a given client application to prompt the user and communicate information about the current value or metric being reported relative to a target, benchmark, or standard of care. For example, if based on the logic of the TMD, the fulfillment of a given discharge that is ordered by a physician is predicted to be significantly delayed, moderately delayed, or negligibly delayed, the client device application can output a display that shows an icon with a particular color determined by and used to communicate the specific categorization of the predicted delay, if any. To provide an example of their use, the icons could appear next to the particular discharge it references among other discharges in a list of pending (yet to be fulfilled) discharge orders. The colored icon, to provide another example, could alternatively appear next to a patient on a user interface that displays all the patients on a given ward; in this exemplary case, the colored icon would communicate the existence of a discharge order (communicated by the icon's presence) and whether the pending discharge is predicted to be at risk for delay, and if predicted to be at risk for delay the category of delay risk (communicated by the icon color). In such scenarios, the color of the icon would serve the purpose of communicating the predicted delay categorization to end users that may be viewing the information.

The performance metric, predictions, and other data generated by inventive system can be accessed via the backend device API and pulled into other third party user facing applications. The data can also be viewed by an authenticated and authorized end user in the graphical user interface of one of the system's client devices. Various views and transformations of the performance metric data can be provided.

The system enables its customers and end users to gain insights about their performance on various metrics of interest and to predict particular outcomes of interest. The customers/end users can slice the data and view it from perspectives that are of particular value to their organization. Within many healthcare organizations a plurality of healthcare workers are involved in the care of a given patient. One benefit of the system is its ability to report relevant data it generates based on relationships between a plurality of related or unrelated healthcare workers and information in the system related to them (for example, any interactions the healthcare workers may have had with specific patients, during particular patient-visits at particular locations or facilities, and various related data or attributes about each of these that the system captures) over particular time ranges of interest. One of the system's client devices that communicates with the backend device can produce a dashboard tailored to the logged in end user's desired settings (i.e. which metrics to show, for what time ranges, etc.) and any restrictions thereof resulting from settings configured by authorized system administrators. End users can have saved views in addition to a system or user set default view. The end user can create ad hoc views as well, and save them as saved views. If the user is authorized and authenticated, he or she can access a dashboard similar to the exemplary dashboard shown in FIG. 29. The end user can interact with the dashboard to view the various metrics from different perspectives (drill up/drill down, change time range, view raw underlying data, etc.). The user can do this using various client device peripherals (touch screen, key board, mouse, microphone—voice commands . . . i.e. voice data that is streamed to a voice to text engine, transcribed, and interpreted by a machine, etc. For example a user could verbally "ask" that particular metric(s) of interest be fetched and shown in accordance with any criteria verbally provided and based upon parsing of the transcript returned, the system would attempt to fulfil the transcribed verbal request). One of the system's client devices can also be configured and used to operate a monitor or television (i.e. a large, flat screen monitor or TV). The client device's controller can run instructions native to the device or remotely received from the backend device to display data and metrics on the large screen graphical user interface. The client device may show a pre-defined sequence of metrics which loops and plays continuously or an authorized end user can interact with the client device via the large screen graphical interface. The large screen graphical user interface can be place in a secured area within a healthcare provider organization where access is controlled and only authorized personnel can enter (for example, an executive suite, physician lounge, operating room, operating room lounge, etc.) and be used to communicate real time data and various performance metrics of interest that are being tracked by the system. The large screen graphical user interface can also be used and controlled by an authenticated and authorized end user during a meeting to display information or be used as a part of a virtual meeting (i.e. a web conference call).

The TMD or a client device running an application that communicates with the TMD can generate a graphical display similar to the exemplary one shown in FIG. 29 which displays an average discharge (D/C) lag for various levels of a healthcare system, as well as the percentage of discharges that had a D/C lag that was at or below goal. Particularly, a client device can request this graphical display from the TMD or the underlying data required to generate it. The TMD can store the D/C lag values or calculate them from data retrieved from the database of the server device. While the D/C lag is the metric shown in FIG. 29, this example is not intended to denote or to imply any limitation to the scope of metrics tracked or generated by the inventive system that may be displayed in a similar report. Moreover, data like that shown in FIG. 29 can also be used to generate performance evaluations of particular personnel (such as nurses or physicians) using a variety of reporting criteria such as patient transaction types, date ranges, etc.

Therefore, the present disclosure concerns machine learning models, the disclosure's application of specific technical techniques that leverage the specific aspects or attributes of particular care transitions in hospital systems in conjunction with the other system components (for example, the RFID tag interaction with the DCE and the DCE's communication with the TMD) that permit the identification of the true state of healthcare facility operations. Moreover, the present disclosure also concerns optimizing throughput in a hospital facility, by helping hospital facilities and their employees, identify potential bottlenecks or waste in the system, be notified about said conditions in real time, make intelligent recommendations, in regards to the allocation of human capital resources capable of potentially mitigating identified waste that are most likely to yield hospital system performance gains related to the handling of what are essentially ubiquitous, common place patient care transitions in any hospital facility. In addition, the present disclosure concerns helping healthcare facilities track performance on specific metrics related to novel new information made available by the system technical embodiments versus facility specific goal performance on these metrics, provide a plurality of projections of said performance statistics ("360 degree view") relevant to different healthcare facility stakeholders, and make available the performance statistic information for managing continuous quality improvement efforts and for incentive system design (to align the incentive of employees with the objectives of the healthcare facility) and objective employee performance assessment.

While only certain features of the invention have been illustrated and described herein, many modifications and changes will occur to those of ordinary skill in the art. The following claims are intended to cover all such modifications and changes.

What is claimed is:

1. A method for predicting an outcome associated with a new patient transaction, the method comprising:
   receiving a plurality of input attributes of the new patient transaction;
   performing pre-processing on the plurality of input attributes to generate an input data set;
   generating an output value from a trained model based upon the input data set; and
   classifying the output value into a delay risk category to predict the outcome.

2. The method of claim 1, further comprising:
   storing a plurality of past patient transactions, each of the plurality of past patient transactions including a plurality of patient attributes and a quantifiable outcome; and
   training a neural network model (NNM) to generate the trained model, wherein the training of the NNM includes:
      performing pre-processing on the plurality of patient attributes for each of the plurality of past patient transactions to generate a plurality of input data sets;
      dividing the plurality of past patient transactions into a first set of training data and a second set of validation data;
      iteratively performing a machine learning algorithm (MLA) to update synaptic weights of the NNM based upon the training data; and
      validating the NNM based upon the second set of validation data,
   wherein the MLA for updating the synoptic weights is one or more of ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), support vector machines, genetic programming, Bayesian statistics, decision trees, case based reasoning, information fuzzy networks, clustering, hidden Markov models, particle swarm optimization, simulated annealing.

3. The method of claim 2, wherein:
   the NNM includes an input layer, output layer, and a plurality of hidden layers with a plurality of hidden neurons; and
   each of the plurality of hidden neurons includes an activation function, the activation function is one of:
   (1) the sigmoid function $f(x)=1/(1+e^{-x})$;
   (2) the hyperbolic tangent function $f(x)=(e^{2x}-1)/(e^{2x}+1)$; and
   (3) a linear function $f(x)=x$,
   wherein x is a summation of input neurons biased by the synoptic weights.

4. The method of claim 2, wherein the NNM is one or more of a feed forward structure Neural Network; ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), and Radial Basis Function Network.

5. The method of claim 2, wherein the performing of the MLA includes measuring a global error in each training iteration for the NNM by:
   calculating a local error, the local error being a difference between the output value of the NNM and the quantifiable outcome;
   calculating the global error by summing all of the local errors in accordance with one of:
   (1) Mean Square Error (MSE) formula $$\frac{\sum_n E^2}{n};$$

(2) Root Mean Square Error (RMS) formula $$\sqrt{\frac{\sum_n E^2}{n}};$$

and
   (3) Sum of Square Errors (ESS) formula $$\frac{\sum_n E^2}{2},$$

wherein n represents a total number of the past patient transactions and E represents the local error.

6. The method of claim 1, wherein the trained model is a trained Self-Organizing Map (SOM) including a plurality of network nodes arranged in a grid or lattice and in fixed topological positions, an input layer with a plurality of input nodes representing the input attributes of the past patient transactions, wherein each of the plurality of input nodes is connected to all of the plurality of network nodes by a plurality of synaptic weights.

7. The method of claim 6, further comprising:
   storing a plurality of past patient transactions, each of the plurality of past patient transactions including a plurality of patient attributes and a quantifiable outcome;
   performing pre-processing on the plurality of patient attributes for each of the plurality of past patient transactions to generate a plurality of input data sets; and
   training a SOM to generate the trained model, wherein the training of the SOM includes:
      initializing values of the plurality of synaptic weights to random values,
      randomly selecting one past patient transaction and determining which of the plurality of network nodes is a best matching unit (BMU) according to a discriminant function, wherein the discriminant function is a Euclidean Distance; and iteratively calculating a neighborhood radius associated with the BMU to determine neighboring network nodes for updating, and updating values of synoptic weights for neighboring network nodes within the calculated neighborhood radius for a fixed number of iterations to generate the trained model.

8. The method of claim 7, wherein normalizing of the plurality of patient attributes includes generating another SOM including the plurality of patient attributes to reduce dimensionality.

9. The method of claim 1, wherein the receiving the plurality of patient attributes of the new patient transaction further includes receiving one or more messages including a patient identification and location information associated with a first RFID tag and a medical professional identification and location information associated with a second RFID tag from a data collection engine (DCE).

10. The method of claim 1, wherein the new patient transaction is one of an admit patient order, discharge patient order, transfer patient order, or room turnover request, and the output value is one of an estimated delay time or an indication of delay or no delay for the new patient transaction.

11. The method of claim 1, wherein:
the receiving of the plurality of patient attributes of the new patient transaction further comprises receiving a plurality of new patient transactions, each including a plurality of patient attributes;
the generating of the output value and classifying the output value further includes generating a graphical image including output values for each of the plurality of new patient transactions;
the method further comprises receiving a graphical display request from a remote client device and transmitting the graphical image to the remote client device as a response;
the trained model is a trained SOM; and
the graphical image is a cluster diagram including a plurality of clusters of output values having a similar characteristic.

12. The method of claim 1, wherein the patient attributes include:
a location of a patient of the new patient transaction received from one of an RFID associated with a patient identification for the patient and a DCE in communication with the RFID;
a medical professional identification of a medical professional associated with the patient received from an RFID associated with the medical professional;
information regarding a prior relationship between the medical professional and the patient received from a memory source;
date information of the new patient transaction;
wherein the receiving of the plurality of patient attributes of the new patient transaction further comprises one or more of the following:
receiving one or more of an age of the patient, insurance information associated with the patient and employment information associated with the patient from a memory source;
receiving information indicative of a medical specialty associated with a facility in which the patient is located from the memory source;

receiving identification information indicative of an individual that signed a patient transaction order and date information of the order from the memory source;
receiving identification information of a current attending physician of record for the patient from the memory source,
receiving information indicating presence or absence of a resident physician as a participant in a patient care episode, and
receiving information indicating a number of medications on a medication administration record at a time of the patient transaction.

13. The method of claim 1, further comprising:
assigning an allocation of appropriate clinical resources to the patient transaction based upon an optimization algorithm in accordance with the delay risk category of the patient transaction and attributes of available clinical resources.

14. A Throughput Manager Device (TMD) comprising:
a transceiver for receiving input attributes associated with a patient transaction from one or more remote entities via a network connection;
the transceiver further for receiving an information request from a remote client access device via the network connection, the information request being a request for calculated quantifiable outcomes for a plurality of patient transactions;
a controller operatively coupled to the transceiver; and
one or more memory sources operatively coupled to the controller, the one or more memory sources storing instructions for configuring the controller to:
calculate a quantifiable outcome for each of the patient transactions from a trained model based upon at least two or more patient attributes of the respective patient transaction where the outcome represents a numerical, continuous or categorical outcome; and
generate an information reply including a graphical display indicating the numerical/continuous output value or the category output of each of the patient transactions.

15. The TMD of claim 14, wherein the one or more remote entities include:
a data collection engine receiving patient identification from a first RFID tag and medical professional identification and location information from a second RFID tag;
a CPOE system;
a Hospital Bed Management System (BMS); and
an Electronic medical records system.

16. The TMD of claim 14, wherein:
the information request further includes a request for an average discharge lag for each of a plurality of facilities in a system, each of a plurality of clinical services lines in a respective facility, and for the system; and
the generating of the information reply including the graphical display further includes including the average discharge lag for each of the plurality of facilities, the each of the plurality of clinical services lines, and for the system in the graphical display.

17. A client access device comprising:
a display;
a transceiver for sending an information request to a TMD via a network connection, the information request being a request for calculated quantifiable outcomes for a plurality of patient transactions based upon a trained model from the TMD;

the transceiver further for receiving the plurality of the calculated quantifiable outcomes from the TMD;

a controller operatively coupled to the transceiver and the display; and one or more memory sources operatively coupled to the controller, the one or more memory sources storing instructions for configuring the controller to:

generate a graphical display on the display indicating a delay risk category of each of the patient transactions based upon the calculated quantifiable outcomes.

18. The client access device of claim 17, wherein:

the memory stores display preferences for selecting metrics to be displayed;

the controller generates the graphical display to include an average discharge lag for a system and each of a plurality of subordinate hierarchical entities and members of the system based upon the display preferences stored in the memory.

19. The client access device of claim 18, wherein:

the controller is coupled to a user input device; and the controller is further configured to interact with the graphical display based upon selections received via the user input device to increase or decrease subordinate hierarchical entities displayed in the graphical display.

* * * * *